(12) United States Patent
Arar et al.

(10) Patent No.: US 11,886,634 B2
(45) Date of Patent: Jan. 30, 2024

(54) PERSONALIZED CALIBRATION FUNCTIONS FOR USER GAZE DETECTION IN AUTONOMOUS DRIVING APPLICATIONS

(71) Applicant: NVIDIA Corporation, Santa Clara, CA (US)

(72) Inventors: Nuri Murat Arar, Zurich (CH); Sujay Yadawadkar, Santa Clara, CA (US); Hairong Jiang, Campbell, CA (US); Nishant Puri, San Francisco, CA (US); Niranjan Avadhanam, Saratoga, CA (US)

(73) Assignee: NVIDIA Corporation, Santa Clara, CA (US)

( * ) Notice: Subject to any disclaimer, the term of this patent is extended or adjusted under 35 U.S.C. 154(b) by 79 days.

(21) Appl. No.: 17/206,585

(22) Filed: Mar. 19, 2021

(65) Prior Publication Data

US 2022/0300072 A1 Sep. 22, 2022

(51) Int. Cl.
*G06F 3/01* (2006.01)
*G06V 10/46* (2022.01)
(Continued)

(52) U.S. Cl.
CPC .......... *G06F 3/013* (2013.01); *G06F 18/2148* (2023.01); *G06F 18/2178* (2023.01);
(Continued)

(58) Field of Classification Search
None
See application file for complete search history.

(56) References Cited

U.S. PATENT DOCUMENTS 10,885,698 B2 1/2021 Muthler et al.
2014/0313129 A1* 10/2014 Elvesjo ................. G06F 1/3231
345/156

(Continued)

OTHER PUBLICATIONS

Wang, Xi, et al. "Tracking the gaze on objects in 3D: How do people really look at the bunny?. " ACM Transactions on Graphics (TOG) 37.6 (2018): 1-18. (Year: 2018).*

(Continued)

*Primary Examiner* — Michelle M Entezari
(74) *Attorney, Agent, or Firm* — Taylor English Duma L.L.P.

(57) ABSTRACT

In various examples, systems and methods are disclosed that provide highly accurate gaze predictions that are specific to a particular user by generating and applying, in deployment, personalized calibration functions to outputs and/or layers of a machine learning model. The calibration functions corresponding to a specific user may operate on outputs (e.g., gaze predictions from a machine learning model) to provide updated values and gaze predictions. The calibration functions may also be applied one or more last layers of the machine learning model to operate on features identified by the model and provide values that are more accurate. The calibration functions may be generated using explicit calibration methods by instructing users to gaze at a number of identified ground truth locations within the interior of the vehicle. Once generated, the calibration functions may be modified or refined through implicit gaze calibration points and/or regions based on gaze saliency maps.

23 Claims, 13 Drawing Sheets

(51) Int. Cl.
*G06V 20/59* (2022.01)
*G06V 40/16* (2022.01)
*G06F 18/214* (2023.01)
*G06F 18/21* (2023.01)

(52) U.S. Cl.
CPC .......... *G06V 10/462* (2022.01); *G06V 20/597* (2022.01); *G06V 40/165* (2022.01); *G06V 40/171* (2022.01)

(56) References Cited

U.S. PATENT DOCUMENTS

| | | | | |
|---|---|---|---|---|
| 2016/0309081 | A1* | 10/2016 | Frahm | G06V 40/19 |
| 2016/0342205 | A1* | 11/2016 | Shigeta | G06V 10/147 |
| 2017/0124391 | A1* | 5/2017 | Invernizzi | A61B 3/0025 |
| 2018/0308252 | A1* | 10/2018 | Alonso | G06F 3/0304 |
| 2019/0101979 | A1* | 4/2019 | Zhang | G06F 3/013 |
| 2019/0265712 | A1* | 8/2019 | Satzoda | G05D 1/0246 |
| 2021/0064128 | A1* | 3/2021 | Alcaide | G06F 3/011 |
| 2021/0173477 | A1* | 6/2021 | Barkman | G06V 40/19 |
| 2021/0350565 | A1* | 11/2021 | Fogelström et al. | G06T 7/251 |
| 2022/0083134 | A1* | 3/2022 | Kassner | G06F 3/013 |
| 2023/0004216 | A1* | 1/2023 | Rodgers | G06V 40/193 |

OTHER PUBLICATIONS

Linden, Erik, Jonas Sjostrand, and Alexandre Proutiere. "Learning to personalize in appearance-based gaze tracking." Proceedings of the IEEE/CVF international conference on computer vision workshops. 2019. (Year: 2019).*

Chen, Wenting, and Xin Sun. "A Non-Contact Human-Computer Interaction Method Based on Gaze." 2023 IEEE 13th International Conference on Electronics Information and Emergency Communication (ICEIEC). IEEE, 2023. (Year: 2023).*

Park, Seonwook, et al. "Few-shot adaptive gaze estimation." Proceedings of the IEEE/CVF international conference on computer vision. 2019. (Year: 2019).*

Valliappan, Nachiappan, et al. "Accelerating eye movement research via accurate and affordable smartphone eye tracking." Nature communications 11.1 (2020): 4553. (Year: 2020).*

"Taxonomy and Definitions for Terms Related to Driving Automation Systems for On-Road Motor Vehicles", National Highway Traffic Safety Administration (NHTSA), A Division of the US Department of Transportation, and the Society of Automotive Engineers (SAE), Standard No. J3016-201609, pp. 1-30 (Sep. 30, 2016).

"Taxonomy and Definitions for Terms Related to Driving Automation Systems for On-Road Motor Vehicles", National Highway Traffic Safety Administration (NHTSA), A Division of the US Department of Transportation, and the Society of Automotive Engineers (SAE), Standard No. J3016-201806, pp. 1-35 (Jun. 15, 2018).

ISO 26262, "Road vehicle—Functional safety," International standard for functional safety of electronic system, Retrieved from Internet URL: https://en.wikipedia.org/wiki/ISO_26262, accessed on Sep. 13, 2021, 8 pages.

IEC 61508, "Functional Safety of Electrical/Electronic/Programmable Electronic Safety-related Systems," Retrieved from Internet URL: https://en.wikipedia.org/wiki/IEC_61508, accessed on Apr. 1, 2022, 7 pages.

Carpenter, R. H. (1988). Movements of the Eyes, 2nd Rev. Pion Limited.

Guestrin, E. D., & Eizenman, M. (2006). General theory of remote gaze estimation using the pupil center and corneal reflections. IEEE Transactions on biomedical engineering, 53(6), 1124-1133.

McLellan, J. S., Marcos, S., Prieto, P. M., & Burns, S. A. (2002). Imperfect optics may be the eye's defence against chromatic blur. Nature, 417(6885), 174-176.

Park, S., Mello, S. D., Molchanov, P., Iqbal, U., Hilliges, O., & Kautz, J. (2019). Few-shot adaptive gaze estimation. In Proceedings of the IEEE International Conference on Computer Vision (pp. 9368-9377).

Arar, N. M. (2017). Robust Eye Tracking Based on Adaptive Fusion of Multiple Cameras (No. Thesis). EPFL.

Krafka, K., Khosla, A., Kellnhofer, P., Kannan, H., Bhandarkar, S., Matusik, W., & Torralba, A. (2016). Eye tracking for everyone. In Proceedings of the IEEE conference on computer vision and pattern recognition (pp. 2176-2184).

Liu, G., Yu, Y., Mora, K. A. F., & Odobez, J. M. (Sep. 2018). A Differential Approach for Gaze Estimation with Calibration. In BMVC (vol. 2, p. 6).

* cited by examiner

PERSONALIZED CALIBRATION FUNCTIONS FOR USER GAZE DETECTION IN AUTONOMOUS DRIVING APPLICATIONS

BACKGROUND

Autonomous and semi-autonomous vehicles leverage machine learning approaches—such as those using deep neural networks (DNNs)—to analyze images of a user to determine various information about a user's gaze. This gaze information may then be used to take responsive action to prevent harm to the user, such as redirecting the user's attention to a potential hazard, pulling the vehicle over, and/or the like. For example, DNNs may be used to detect that a driver is falling asleep at the wheel, based on the user's downward gaze toward the floor of the vehicle, which may lead to an adjustment in the speed and direction of the car (e.g., pulling the vehicle over to the side of the road) or an auditory alert to the driver. However, determining a gaze of a person can be difficult, given that each individual has such different measurements with respect to their eyes (e.g., angular offset between visual and optical axes of an eyeball, cornea radius and curvature, distance between pupil center and corneal center, refraction of aqueous humor and cornea) and/or other facial features in addition to different heights, seating positions, and/or other posture information that may affect the accuracy of the DNNs deployed to detect the user's gaze.

For example, conventional systems often rely on training DNNs with a high volume of training image data that captures the facial features of different individuals to ensure that gaze predictions are accurate across all drivers. However, this methodology is problematic for a number of reasons. For instance, a trained DNN may be trained using training data that is skewed toward one portion of the general population and, consequently, may fail to make accurate gaze predictions for other portions of the general population. Similarly, while the training data for a DNN may capture the images of several different individuals, the training data may not include the same individual with differing eyewear. Likewise, a trained DNN that provides faulty gaze predictions will continue to provide inaccurate gaze predictions unless it is retrained with images from the specific driver, which inconveniences the driver and is difficult to implement using the on-board computing resources in a vehicle. Yet, automobile manufacturers are unlikely to release autonomous vehicles using DNNs, especially in situations involving long stretches of uninterrupted driving, until a high level of safety and accuracy with respect to predicting the driver's gaze are achieved. As a result, competing interests of safety and accuracy make generating a practical, sound, and reliable gaze prediction system within an autonomous vehicle increasingly onerous.

SUMMARY

Embodiments of the present disclosure relate to personalized calibration functions for user gaze detection in autonomous driving applications. Systems and methods are disclosed that provide more accurate gaze predictions through the use of generated or learned calibration functions that are personalized for particular users through explicit and/or implicit calibration. As such, embodiments of the present disclosure relate to fine-tuning gaze predictions of users in autonomous driving machines by generating calibration functions through explicit instruction to the user to gaze at certain ground truth locations and/or analysis of a user's historical viewing habits using—for example—gaze saliency maps.

In contrast to conventional systems, such as those described herein, the systems of the present disclosure may generate calibration functions for a particular user and fine tune or update predicted gaze information—e.g., predicted using a deep neural network (DNN)—using the personalized calibration functions. As a result, instead of following a cumbersome and time-consuming process of training or re-training a DNN using a large set of images of a particular user, gaze predictions for a user may instead be refined and adjusted using personalized calibration functions—which may be generated using explicit and implicit calibration methods—during deployment of the DNN. Thus, in a scenario where a DNN has been trained using a diverse set of data (of other users), the accuracy of the DNN is bolstered through the use of personalized calibration functions for a particular user. Additionally, since vehicles for personal use are likely to be operated by a small set of users that is stable in size and frequency of use, the likelihood that the personalized functions are highly attuned to and precise for each user are further improved. Moreover, for those users with privacy concerns, the generation of personalized calibration functions using in-car functionality avoids the transmission of personal or biometric information to other entities which may operate outside the vehicle to accomplish tuning to a user or a subset of users.

As such, by using personalized calibration functions, gaze predictions that are specific to an identified user may be calculated with little burden on computing resources, leading to higher accuracy in gaze predictions for a user, reduced time to compute a gaze prediction with a high level of accuracy, higher availability of computing resources to perform other functions, and improved outcomes in decision-making based on a user's predicted gaze direction or location.

BRIEF DESCRIPTION OF THE DRAWINGS

The present systems and methods for personalized calibration functions for user gaze detection in autonomous driving applications are described in detail below with reference to the attached drawing figures, wherein.

DETAILED DESCRIPTION

Figure 1A:
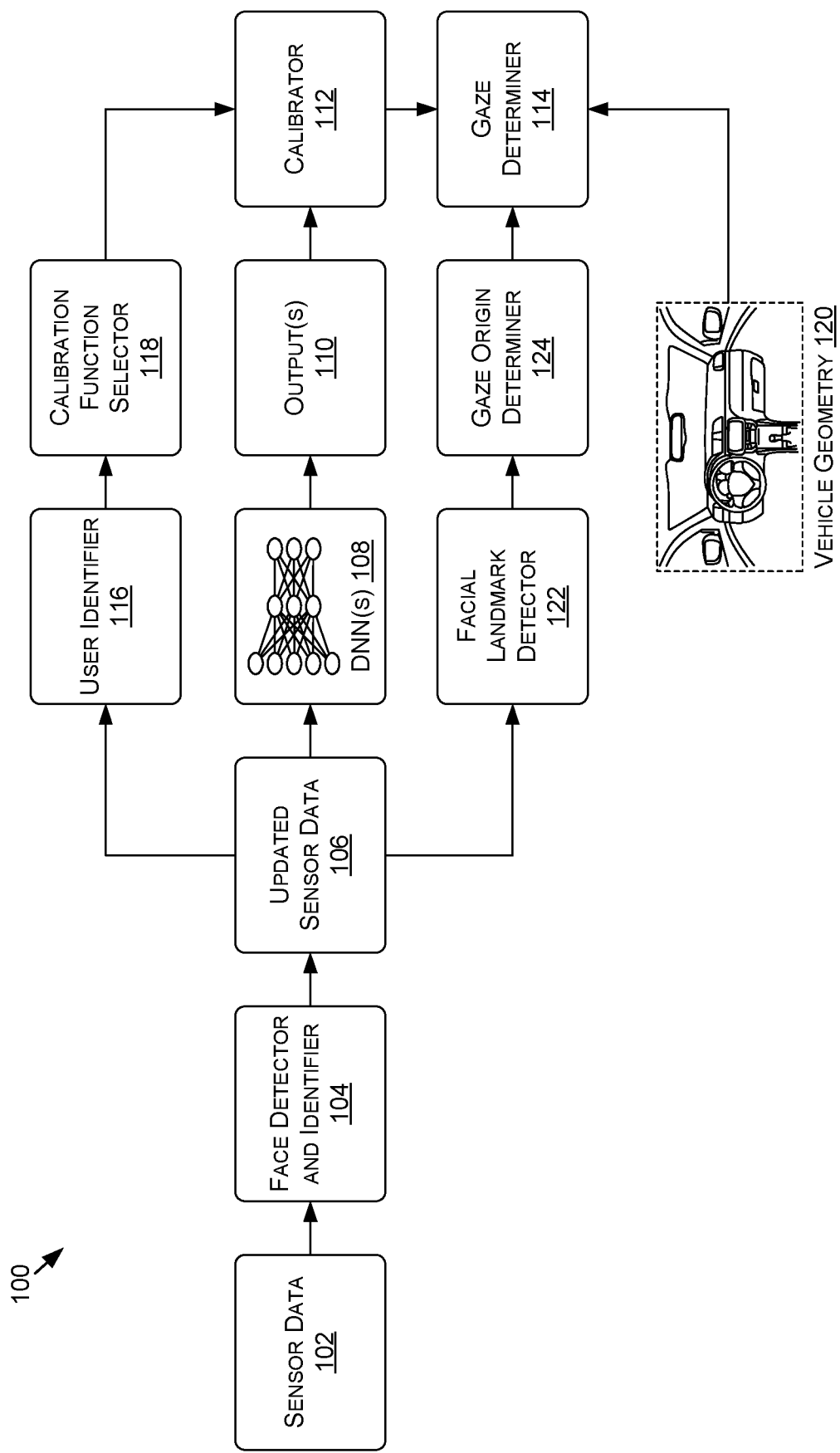
FIG. 1A is a data flow diagram illustrating an example process for applying personalized calibration functions to gaze predictions determined by a machine learning model, in accordance with some embodiments of the present disclosure.

Embodiments of the present disclosure relate to personalized calibration functions for user gaze detection in autonomous driving applications. Although the present disclosure may be described with respect to an example autonomous vehicle 600 (alternatively referred to herein as "vehicle 600" or "ego-vehicle 600," an example of which is described herein with respect to FIGS. 6A-6D), this is not intended to be limiting. For example, the systems and methods described herein may be used by non-autonomous vehicles, semi-autonomous vehicles (e.g., in adaptive driver assistance systems (ADAS)), vehicles in combination with trailers, piloted and un-piloted robots or robotic platforms, warehouse vehicles, off-road vehicles, flying vessels, boats, shuttles, emergency response vehicles, motorcycles, electric or motorized bicycles, aircraft, construction vehicles, underwater craft, drones, and/or other vehicle types. In addition, although the present disclosure may be described with respect to autonomous driving, this is not intended to be limiting. For example, the systems and methods described herein may be used in robotics, aerial systems, boating systems, and/or other technology areas, such as for in-cabin and/or external perception, control decision determinations, path planning, obstacle avoidance, driver or occupant warning systems, and/or other processes. In some embodiments, the systems and methods described herein may be used to estimate head pose information, recognize and detect emotions of users, classify features of user(s), and/or the like. For example, although primarily described herein with respect to gaze estimation, the systems and methods of the present disclosure may be used to fine-tune or personalize neural networks, machine learning models, and/or the outputs thereof. Similarly, the systems and methods described herein may be used to personalize and/or refine speech and visual recognition for a user(s).

In contrast to conventional systems, such as those described herein, the system of the present disclosure generates and applies personalized calibration functions to gaze predictions—e.g., such as those computed using a machine learning model (e.g., a deep neural network (DNN)—to determine a personalized gaze prediction for a particular user. In turn, the personalized or updated gaze prediction may be used to determine responsive actions by an autonomous vehicle. As a result, the accuracy of determining gaze predictions—such as whether a user's gaze direction that is mapped externally to the vehicle indicates the user has seen a road hazard—increases, thereby leading to more appropriate and meaningful responsive actions. For instance, the machine learning model may provide a gaze prediction (e.g., gaze vector, angular offset, or values in the three-dimensional world coordinates of the vehicle) of a user using data collected by sensors in a vehicle. A calibration function, unique to the user, may then be applied to the gaze prediction values. The calibration functions may be generated by calculating an offset from calculated gaze predictions in comparison to sensor data associated with ground truth locations (e.g., 3D locations in the vehicle that the user is asked to look at). Once generated, the calibration function may be incorporated into various stages of post-training of the machine learning model. After the calibration function has been applied, updated gaze predictions may be calculated and used to determine where a user is looking internal to or external to the vehicle, thereby providing a gaze prediction that is tailored to the user without the need for retraining the machine learning model.

In embodiments of the present disclosure, and to ultimately generate highly accurate gaze predictions tailored to a particular user, a calibration function (e.g., functions that reconcile values from gaze predictions to match data collected when a user was looking at ground truth locations) that corresponds to a particular user may be generated. A set of ground truth locations (e.g., locations within a three-dimensional world coordinate system in the vehicle) may be identified. Ground truth locations may span the user's view from left to right and/or front to back and include locations such as a rear-view mirror, a side-view mirror, a portion of a windshield, an instrument cluster, a user interface, or a camera sensor. Once the ground truth locations have been identified, the user may be instructed to look at each of the ground truth locations for a short time to allow a sensor in the vehicle to capture data such as images of the user (e.g., images of the user's facial landmarks either separately or in combination). Using the collected data, the machine learning model may generate a gaze prediction for the user, which may include a predicted gaze location within the vehicle (e.g., a point in the 3D world coordinate system of the vehicle), a predicted gaze vector (which may be projected from a determined gaze origin of the user to identify a point in the 3D world coordinate system), and/or an offset angle. The predicted gaze locations may then be compared to the ground truth locations (or associated data) in order to determine offsets between the predictions of the machine learning model and the known gaze locations of the user. These offsets may be used to generate a calibration function that may be used in deployment of the machine learning model for refining predictions of (or updating values of one or more layers of) the machine learning model to increase the gaze predictions for the particular user.

In some embodiments, in addition to or alternatively from explicit user calibration (e.g., prompting the user to look at predetermined 3D locations within the vehicle), the calibration function may also be refined or modified by implicitly tracking the user's gaze. This may be executed, in embodiments, using gaze saliency regions to determine 3D locations within the vehicle for which to perform calibration for the particular user. For instance, over time, gaze saliency maps may be generated, gaze calibration points may be identified from commonly gazed upon regions or points within the vehicle, and these gaze calibration points may be used similarly to the explicit calibration points to compute and/or update the calibration functions for the user. For example, because the explicit gaze locations may not be commonplace gaze locations for a user during operation of a vehicle, the gaze saliency maps may be used to identify locations within the vehicle that may be good candidates for calibration due to the increased likelihood of the user gazing at that particular location during operation. As such, the gaze saliency maps may be used to define one or more regions or points within the vehicle that are candidates for implicit calibration. In this way, the calibration functions for the user may be generated and/or updated in real-time during deployment of the machine learning model, such that changes to the user (e.g., appearance, posture, position, etc.) may be accounted for and used to increase the accuracy of gaze location or direction predictions. In some embodiments, the calibration functions may be specific to particular areas or gaze locations within the vehicle (e.g., a different calibration function for a side-view mirror versus a rear-view mirror), or may only be used for particular areas or gaze locations within the vehicle. For example, a general gaze direction or location may be determined, and if the gaze location or direction falls within one of the calibrated or predefined regions, a calibration function may be applied to the output of the machine learning model. In contrast, where the gaze region or location is not included in the calibrated regions, the calibration function may not be used and the output of the machine learning model may be used directly without applying a calibration function. Likewise, the user may be able to activate the use of calibration functions based on the region of the vehicle that the user is viewing (e.g., calibration functions are used only when the user is gazing at the rear-view mirror).

In some embodiments, explicit and/or implicit calibration techniques are applied in multiple stages. For instance, explicit calibration of a user's gaze and/or other features may take place at the location of the point of sale (e.g., location where the user has purchased the item such as a dealership of the vehicle) and/or at the location when a change in possession occurs (e.g., the location at which a user takes possession). For example, the user may be asked to spend a predetermined amount of time in the vehicle to allow for collection of data (e.g., video, image, audio, and/or gaze data). The user may be asked to look at locations that are specially marked within the vehicle to aid in collecting data. In some embodiments, the location where the point of sale or change in possession is taking place may have specialized equipment (e.g., special devices that determine eye or gaze measurements) that is used to collect data about the user. In this way, the system within the vehicle may be programmed to provide non-calibrated or personalized gaze predictions, based on a DNN trained with a diverse set of data, prior to sale of the vehicle. Once sold or exchanged, the vehicle may collect data regarding the operating user, generate personalized calibration functions, and refine the functions as additional data about the user is collected. Additional calibration may take place once the user operates the vehicle for the first time through the use of additional specialized markers, voice prompts, and/or storage of user adjustments (e.g., adjustments to seat position). During everyday use, the personalized calibration functions may be refined using implicit calibration techniques. For instance, data collected on a daily basis when the user gazing at specialized locations (e.g., locations that are often viewed by all users such as a rear-view mirror) may be used to calibrate the user's personalized calibration functions. In some embodiments, such as where one or more of the above stages are not completed, gaze saliency maps may be used to generate and/or refine personalized calibration functions, as described herein.

In some embodiments, once the calibration function is trained or learned, the user's gaze may be determined by applying the calibration function to the output of the machine learning model and/or to values in a layer (e.g., a last layer) of the machine learning model to generate an updated output of the machine learning model. For instance, when a user enters the vehicle, the user's facial landmarks may be detected to identify the user, and a calibration function that corresponds to the user may be retrieved or employed. The machine learning model may then process sensor data captured that depicts the user, such as facial landmarks, via a sensor. Data captured by the sensor may include images of a user's face, eyes, and other facial landmarks. Using the collected data, the machine learning model may determine a gaze prediction for the user. The gaze prediction may be represented through a variety of values, including 3D coordinates (within a fixed coordinate system of a vehicle) indicative of the user's gaze location, an angular offset of the user's gaze, or a gaze vector (which may be projected from a detected gaze origin). In some embodiments, the machine learning model may calculate a gaze origin in the 3D coordinate space of the vehicle to aid in determining the user's gaze location—e.g., such that the gaze vector may be localized to the gaze origin to determine the final gaze location direction and/or estimate). The machine learning model may then apply the personalized calibration function to the gaze prediction values to generate an updated set of values (e.g., updated values in the 3D world coordinates of the vehicle, updated angular offset, updated gaze vector, etc.) that more accurately represents the gaze of the user.

The calibration function may be applied at different stages of post-processing depending on the embodiment. For example, the calibration function may be applied after the machine learning model has output a set of gaze prediction values (e.g., raw gaze prediction). In some embodiments, the calibration function may operate on raw gaze prediction values themselves. However, the calibration function may also be applied to the values—e.g., a vector or tensor—from a layer(s) of the machine learning model, and these updated or calibrated values may then be used to compute the final prediction of the machine learning model with respect to the 3D location, gaze vector, angular offset, and/or other gaze prediction type.

With reference to FIG. 1A, FIG. 1A is a data flow diagram illustrating an example process 100 for applying personalized calibration functions to gaze predictions determined by a machine learning model, in accordance with some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory.

The process 100 may include generating and/or receiving sensor data 102 from one or more sensors of a vehicle 600 (which may be similar to the vehicle 600, or may include non-autonomous or semi-autonomous vehicles). The sensor data 102 may be used within the process 100 for identifying faces, facial landmarks, eye information, and/or other information of one or more occupants of the vehicle 600, identifying an occupant(s) based on facial features, detecting gaze of an occupant(s) of the vehicle 600, generating outputs 110 using one or more deep neural networks (DNNs) 108, applying personalized calibration functions to a layer(s) of DNN(s) 108 or to output(s) 110, determining gaze location of occupant(s) within a three-dimensional world coordinate system corresponding to the interior of the vehicle 600, generating calibration functions based on offsets calculated by comparing ground truth locations and/or implicit calibration points and regions against gaze prediction values calculated by DNN(s) 108, determining one or more actions to take based on the calibrated gaze prediction, and/or other tasks or operations. The sensor data 102 may include, without limitation, sensor data 102 from any type of sensors, such as but not limited to those described herein with respect to the vehicle 600 and/or other vehicles or objects—such as robotic devices, VR systems, AR systems, mixed reality systems, etc., in some examples. As a non-limiting example, and with reference to FIGS. 6A-6C, the sensor data 102 may include the data generated by, without limitation, RADAR sensor(s) 660, ultrasonic sensor(s) 662, LIDAR sensor(s) 664, microphone(s) 696, stereo camera(s) 668, wide-view camera(s) 670 (e.g., fisheye cameras), infrared camera(s) 672, surround camera(s) 674 (e.g., 360 degree cameras), long-range and/or mid-range camera(s) 698, in-cabin cameras, in-cabin heat, pressure, or touch sensors, in-cabin motion sensors, in-cabin microphones, and/or other sensor types.

In some embodiments, the sensor data 102 may correspond to sensor data generated using one or more in-cabin sensors, such as one or more in-cabin cameras, in-cabin near-infrared (NIR) sensors, in-cabin microphones, and/or the like. The sensor data 102 may correspond to sensors with a sensory field or field of view internal to the vehicle 600 (e.g., cameras with the occupant(s), such as the driver, in its field of view). In some embodiments, the sensor data 102 may also correspond to sensor data generated using one or more external sensors of the vehicle 600, such as one or more cameras, RADAR sensor(s) 660, ultrasonic sensor(s) 662, LIDAR sensor(s) 664, and/or the like. As such, sensor data 102 may also correspond to sensors with a sensory field or field of view external to the vehicle 600 (e.g., cameras, LiDAR sensors, etc. with sensory fields including the environment exterior to the vehicle 600).

Figure 2A:
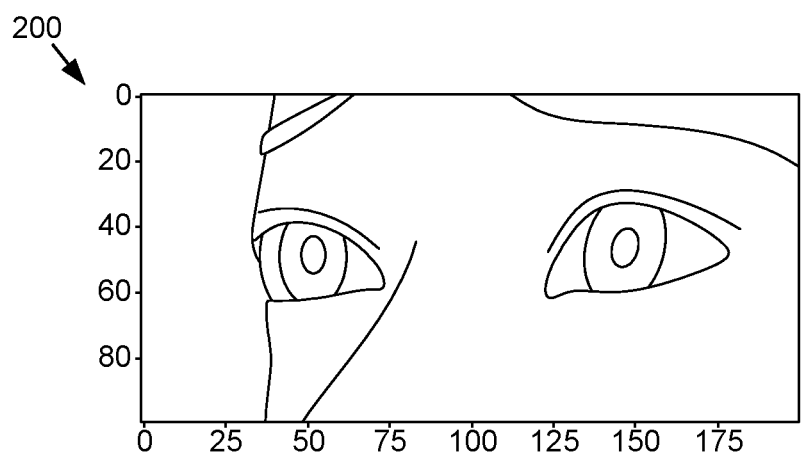
FIGS. 2A-2B are example illustrations of sensor data of a user's facial features used predict a user's gaze, in accordance with some embodiments of the present disclosure.
Figure 2B:
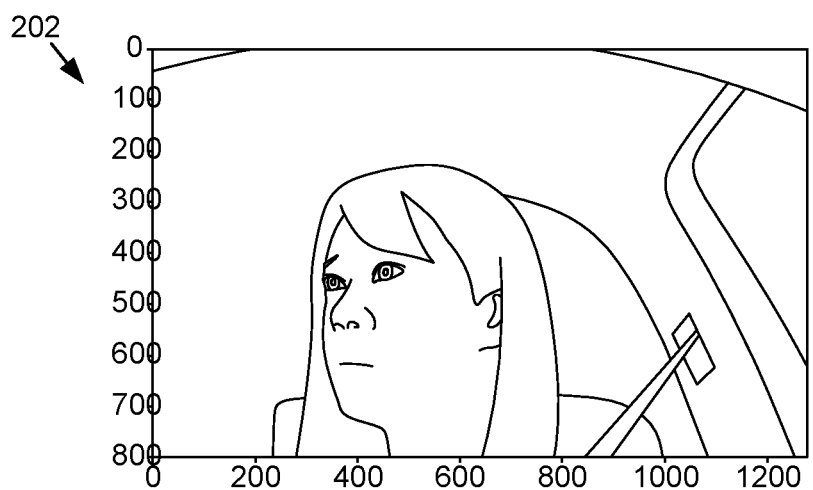

With respect to FIGS. 2A-2B, images 200 and 202 include example images representing sensor data 102 of an occupant—e.g., more focused on eyes of the user in the image 200 and more broadly focused on a face of the user in the image 202. The sensor data 102, as illustrated in this example, may include coordinate information regarding the user's facial features. For instance, image 200 and image 202 show (x, y) locations of the head and/or facial features (e.g., eyes, nose, and mouth) of the user, which may be used in determine a gaze prediction for the user.

Turning back to FIG. 1A, the face detector and identifier 104 may analyze the sensor data 102 to detect a face(s) of a user(s) in the vehicle. The face detector and identifier 104 may also identify and denote which portion(s) of the sensor data 102 includes a face(s) of the occupant(s). For example, if the sensor data 102 includes an image of a user, the face detector and identifier 104 may determine that a face exists within the sensor data 102 and denote which pixels—or a bounding shape defining the same—of the image include the face or facial features of the user. The face detector and identifier 104 may execute one or more machine learning algorithms, deep neural networks, computer vison algorithms, image processing algorithms, mathematical algorithms, and/or the like to determine whether a face exists within sensor data 102 and/or which portion of the sensor data 102 includes the face.

The face detector and identifier 104 may also generate updated sensor data 106 by modifying the sensor data 102 to focus on a face(s) or facial features of a user(s). For instance, once the face detector and identifier 104 has identified portions of the sensor data 102 that correspond to the face or facial features of the occupant(s), the sensor data may be modified (e.g., cropped, warped, rotated, zoomed, reflected, dilated, sheared, translated) to generate updated sensor data 106. For example, the face detector and identifier 104 may crop an image of an occupant in sensor data 102 to only show specific facial features of the occupant. In some embodiments, the face detector and identifier 104 may detect faces of multiple occupants in sensor data 102 and modify sensor data 102 to isolate each detected face. For example, if the sensor data 102 includes an image with five detected faces, the face detector and identifier 104 may identify pixels pertaining to each occupant in the image. Based on the identified pixels, the face detector and identifier 104 may crop the image five times to generate updated sensor data 106 that includes a separate image containing pixels for each detected face. The updated sensor data 106 may, in embodiments, correspond to the sensor data 102, such as where the sensor data 102 is not updated or altered. As such, sensor data 102 and/or updated sensor data 106 may be used interchangeably, in some embodiments.

Referring again to FIGS. 2A-2B, FIG. 2B is an example of an image represented by the sensor data 102 that depicts an image of a face of an occupant, and FIG. 2A may correspond to an example of updated sensor data 106 that represents a cropped version of FIG. 2B to isolate a set of facial features. The image 202 may include the user's entire face and thus may include the user's eyes, ears, hair, nose, and mouth. In this example, the face detector and identifier 104 may detect a face of the user in the image 202 and identify pixels or a region of the image 202 that include only the eyes and immediate surrounding area of the occupant. Based on this identification of pixels, the face detector and identifier 104 may crop the image 202 to form the image 200, which only includes the user's eyes and the area immediately surrounding the user's eyes. The image 200, which is a cropped version of the image 202, may correspond to the updated sensor data 106 that may be further analyzed to determine facial landmarks, the identity of the user, and predicted gaze, among other things.

Turning back to FIG. 1, the updated sensor data 106 may then be used by a user identifier 116 and/or calibration function selector 118 to identify a user and retrieve a calibration function(s) associated with the user. The updated sensor data 106 may also be used to by DNN(s) 108 to generate outputs with respect to gaze predictions. Similarly, the updated sensor data 106 may be analyzed by facial landmark detector 122 to determine facial landmarks (e.g., eyes, nose, mouth, etc.) that aid gaze origin determiner 124 in determining an origin of the user's gaze. Where updated sensor data is used, the updated sensor data may be different for different components, features, or functionality. For a non-limiting example, the DNN(s) 108 may process updated sensor data 106 corresponding to eyes of a user, the user identifier 116 may process updated sensor data 106 corresponding to an entire face and upper torso of a user, and the facial landmark detector 122 may process updated sensor data 106 corresponding to a face of the user.

A calibrator 112 may apply calibration functions associated with a user to outputs 110 or use the calibration functions to operate on a layer (e.g., a last layer) of the DNN(s) 108 to provide updated gaze prediction information or values. Using three-dimensional vehicle geometry 120 and updated gaze prediction information or values from the calibrator 112, a gaze determiner 114 may determine a location or direction that the user is gazing within the vehicle. Based on the gaze prediction, responsive actions—such as slowing down when a user is inattentive or maneuvering around a road hazard that the user has not seen—may be taken.

The user identifier 116 may determine the identity of a user(s) or an occupant(s) of a vehicle based on the updated sensor data 106. For instance, the user identifier 116 may analyze facial features present in the updated sensor data 106, identify relationships between the facial features, and identify a user profile that corresponds to the facial features and/or relationships between facial features. The user profile may contain a variety of information regarding the user such as characteristic facial features, relationships between those features, gaze saliency maps, and/or regions associated with the user's viewing habits, personal information, associated calibration functions, and/or the like.

The calibration function selector 118 may retrieve calibration functions associated with an identified user or occupant. A calibration function may operate on gaze prediction values and/or features of an image, as determined using DNN(s) 108, based on offsets calculated for a particular user in order to provide more accurate and personalized gaze predictions. In some embodiments, the calibration function may be associated with a particular region of the vehicle. For example, a calibration function may only apply to a region encompassing a rear-view mirror and the immediate surrounding area. In some embodiments, when a user is determined to be gazing in the region including the rear-view mirror, a calibration function corresponding to that region may be selected and applied. Likewise, a calibration function that applies to all regions of the vehicle may be used. In some embodiments, a user may identify which regions within the vehicle may use calibration functions to update gaze prediction values. For example, a user may be able to identify one or more regions, such as a region encompassing a side-view mirror, to use calibration functions for. In such an example, when the user gazes at the region including the side-view mirror, the calibration functions are then applied to calculated gaze prediction values. In some embodiments, one or more calibration functions may be targeted toward user-specific attributes. For example, one or more calibration functions may be associated with particular conditions, such as a user's eyewear or seat position, and applied to gaze prediction values when one or more conditions are met.

The calibration functions may be calculated using explicit calibration methods, in embodiments. For instance, the user may be instructed to gaze at a set of ground truth locations within a vehicle. As the user gazes at each point, gaze predictions, such as a predicted gaze location within a three-dimensional world coordinate system in the vehicle, may be generated using the process 100. The number of ground truth locations used to generate calibration functions may be increased or decreased depending on the geometry and size of the vehicle. The predicted gaze location (e.g., output(s) 110), as calculated by the process 100, may be compared with the ground truth locations in order to calculate an offset to adjust the predicted gaze location. For example, the user may be instructed to gaze at a particular side view mirror, as a designated ground truth location. While the user is gazing at the side-view mirror, the process 100, including DNN(s) 108, may generate a predicted gaze location using the sensor data 102 and/or updated sensor data 106 captured while a user was gazing at the ground truth location. For example, the user's predicted gaze location may be two inches to the left of the side view mirror. Based on the difference between the user's predicted gaze location and the ground truth location (which is the side-view mirror in this example), an offset may be calculated to adjust the predicted gaze location to the ground truth location. Based on the offset calculated when comparing computed gaze locations to ground truth locations (or associated data), one or more calibration functions may be computed. In some embodiments, the calibration functions may be specific to a particular region within the vehicle (e.g., an area around a side-view mirror) or may be used for all points within the vehicle.

In some embodiments, comparing ground truth location(s) and/or gaze prediction(s) within the vehicle may involve a process of converting coordinates within a three-dimensional coordinate system from the perspective of a sensor (e.g., camera) into coordinates within a three-dimensional world coordinate system in the vehicle. For instance, the gaze prediction may be calculated within a three-dimensional coordinate system corresponding to a sensor and may be converted into coordinates in the three-dimensional world coordinate system in the vehicle before comparing the predicted gaze location with the ground truth locations. The conversion may also take place in the opposite direction as well (e.g., ground truth location coordinates in the three-dimensional world coordinate system in the vehicle may be converted into coordinates in the three-dimensional coordinate system from the perspective of the sensor). In some embodiments, the conversion from one coordinate system to another takes place with other types of gaze information, such as vectors and/or angular offsets. In some embodiments, explicit calibration points within the vehicle may be selected within the camera coordinate system and then converted into the vehicle coordinate system.

Figure 3A:
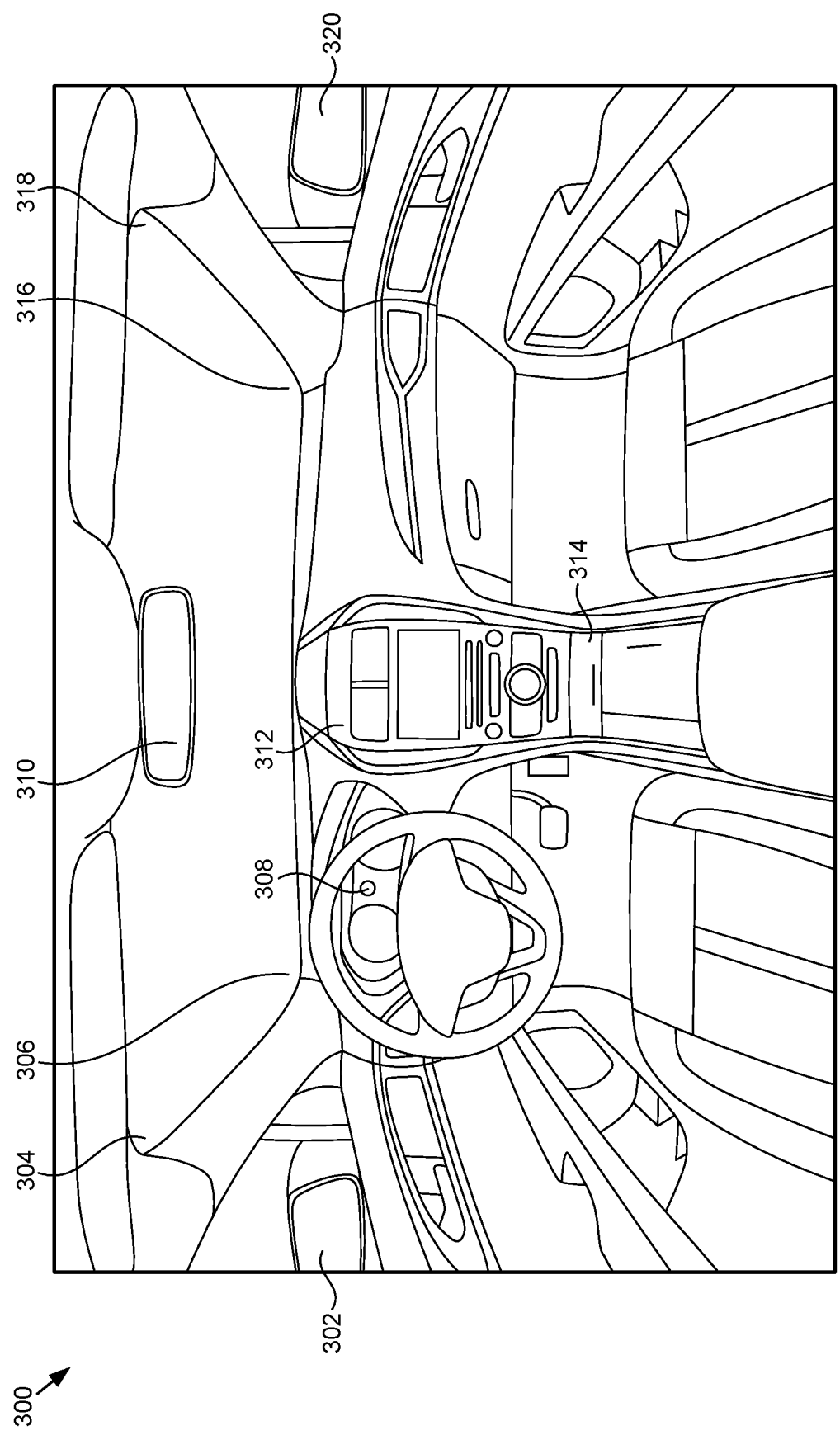
FIG. 3A is an example illustration of a vehicle's interior with calibration points that a user is explicitly instructed to gaze at during an explicit calibration process, in accordance with some embodiments of the present disclosure.

As an example of explicit calibration, and with respect to FIG. 3A, FIG. 3A is an example illustration of a vehicle's interior with calibration points that a user is explicitly instructed to gaze at during an explicit calibration process. The vehicle interior 300 includes ten ground truth locations points (e.g., ground truth locations 302, 304, 306, 308, 310, 312, 314, 316, 318, 320). The ground truth locations include particular areas of the vehicle, such as ground truth locations 302 and 320 that are associated with side-view mirrors. Likewise, the ground truth location 308 includes a sensor (e.g., camera) that captures sensor data 102. Once the ground truth locations have been determined, the user may be instructed to look at each point, such as ground truth location 312, while the process 100 calculates a gaze prediction (e.g., output(s) 110). The gaze prediction may be further processed to determine a predicted gaze location for each of the ground truth locations. The predicted gaze location for each of the ground truth locations may be converted from coordinates in a coordinate system associated with the sensor to coordinates in a coordinate system associated with the vehicle. Once converted, the predicted gaze location for each ground truth location is compared against the ground truth location coordinates (or other gaze information) to calculate offsets, which are, in turn, used to calculate one or more calibration functions. In this example, a separate calibration function is generated for each of the ten ground truth location areas and is applied when the user is predicted to be gazing at a region encompassing a ground truth location (e.g., a region surrounding ground truth location 310 indicating a rear-view mirror).

Turning back to FIG. 1A, the calibration functions may be modified or refined by tracking the user's gaze implicitly using methods similar to that of explicit calibration. For instance, based on information regarding how frequently a user looks at different regions within a vehicle, those regions may be used to implicitly calibrate the generated calibration functions. In some embodiments, gaze information regarding a user may be tracked over some period of time to generate gaze saliency maps. The gaze saliency maps, or heat maps, indicate where a user gazes at more frequently than other regions of a vehicle. For example, an area of the vehicle that includes a commonly viewed vehicle feature, a rear-view mirror, may have a darker region within a gaze saliency map in comparison to a less commonly viewed vehicle feature, such as an upper region of a windshield. In some embodiments, a gaze saliency map may be created using a coordinate system that is shared with other gaze information, such as implicit gaze calibration regions and/or points. In some embodiments, the calibration functions are generated using the explicit calibration method described herein prior to applying implicit calibration techniques.

Figure 3B:
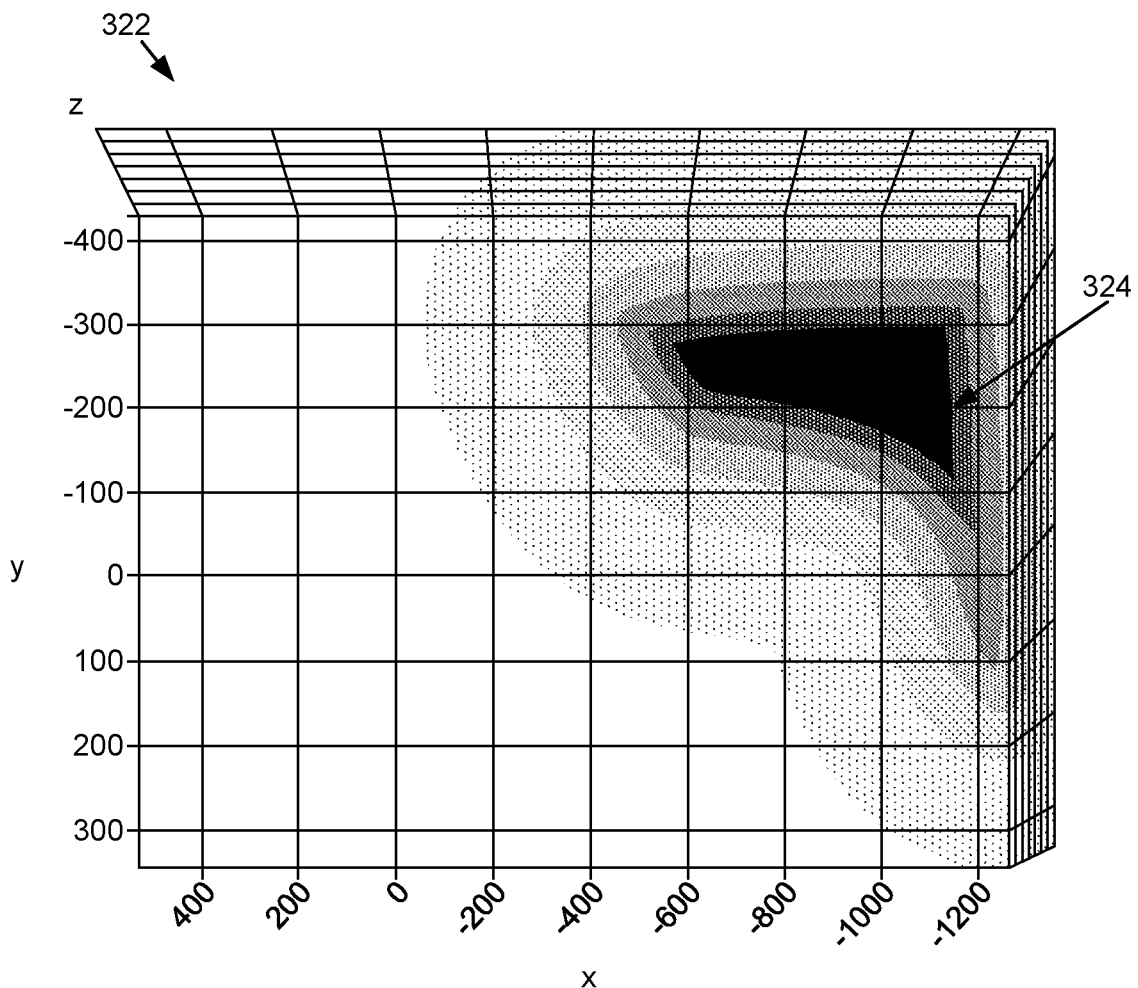
FIG. 3B is an example gaze saliency map corresponding to the vehicle's interior which indicates the frequency with which the user gazes at each location, in accordance with some embodiments of the present disclosure.

Turning to FIG. 3B, FIG. 3B is an example gaze saliency map corresponding to a vehicle's interior indicating the frequency with which the user gazes at those locations within the vehicle. Gaze saliency map 322 is a heat map for gaze frequency with respect to the top right of the vehicle interior (e.g., on the passenger side of the vehicle). As shown in gaze saliency map 322, portions of the vehicle interior have darker regions corresponding to more frequent gaze locations than those regions that are lighter or have less dense patterns of points. In this example, region 324 has the densest pattern of points and indicates an area of frequent gazing by the particular user as determined by using historical data of the user's viewing habits. For example, with respect to the gaze saliency map 322—where the coordinate system is similar to that of implicit gaze calibration region map 326—the gaze saliency map 322 may indicate that the user has more frequently gazed toward the right front gaze region 338 than other gaze regions. In some embodiments, weighting may be applied to give more weight to more recent gaze information when generating the gaze saliency map 322. The gaze saliency map 322 may then represent the user's viewing behaviors, patterns, and/or frequency, which may be used to determine implicit calibration ground truth points that may be used to generate, update, and/or fine-tune a calibration function for a particular user.

Turning back to FIG. 1A, using the gaze saliency maps, implicit gaze calibration regions and/or points may be determined. For instance, a high density pattern of points (e.g., an area that is highly viewed by a user) may be used to form boundaries for an implicit gaze calibration region. For example, if the gaze saliency map includes a cluster of points around the center of the windshield, then an implicit gaze calibration region around that area may be used to calibrate the user's predicted gaze location. In some embodiments, an implicit gaze calibration point may be generated from one or more gaze saliency maps. Because the saliency maps include information regarding the user's habits, the maps may produce regions or points within the vehicle interior that are less commonly looked at by other users. For example, many users may not look at a rear-view mirror if a back-view camera has been installed for use when the vehicle is in reverse, but the saliency map for a particular user may still show the user gazing at the rear-view mirror and each side-view mirror frequently in quick succession of each other.

When a user gazes in a region, as determined from gaze saliency maps, calibration function(s) associated with the user may be modified or refined. For instance, if a user frequently views a particular region in the vehicle, predicted gaze locations that are near, but not quite within an implicit gaze calibration region may be used to adjust the associated calibration functions. For example, if a user adjusts seat positioning and gazes at an implicit gaze calibration region, a predicted gaze location of the user may be near the edge of the implicit gaze calibration region, but not within the boundaries of the region. Given the offset between the implicit calibration region boundaries and the predicted gaze location, the calibration function(s) associated with the user may be adjusted to more accurately reflect the user's gaze. In some embodiments, offsets calculated across several implicit calibration regions may be used to refine one or more calibration functions. In some embodiments, offsets calculated using implicit calibration regions may be applied to calibration functions associated with a particular region of the vehicle.

In some embodiments, triggering events may also be used to determine whether a user is gazing at or near an implicit gaze calibration region. For instance, if a user historically places the vehicle in reverse and then gazes at the center console, then the detection of a predicted gaze location in the implicit gaze calibration region may be associated with a triggering event of placing the vehicle in reverse. In some embodiments, the user's predicted gaze location with respect to a particular region may be verified based on the occurrence of a triggering event. For example, in a scenario where a user historically gazes at a center console after placing the vehicle in reverse mode and the user recently adjusted seat positioning, placing the vehicle in reverse would cause an automatic verification process to determine whether a predicted gaze location (using sensor data captured shortly after placing the vehicle in reverse) falls within the implicit gaze calibration region. In this example, the user's predicted gaze location may be verified to determine whether the user is gazing within an implicit gaze calibration region surrounding the center console. If the predicted gaze location is several inches outside of the implicit gaze calibration region around the center console (due to the user adjusting seat positioning), then offsets between the predicted gaze location and points within the implicit calibration region surrounding the center console may be calculated. Using the offsets, the calibration functions for the user may be adjusted to reflect that the user is gazing at the center console within the implicit calibration region.

Figure 3C:
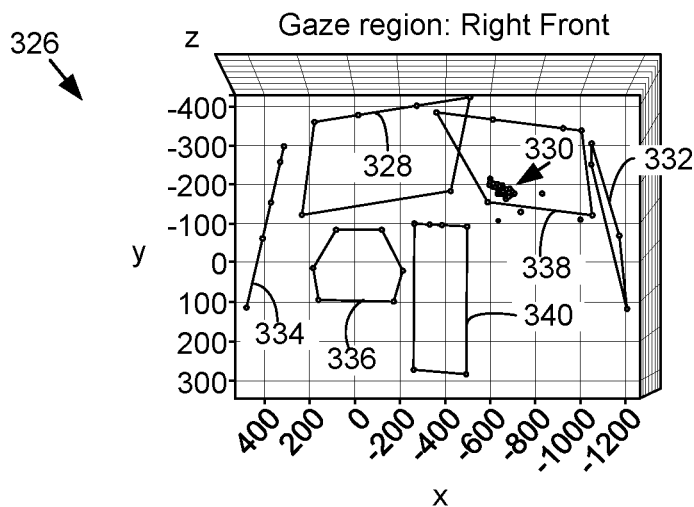
FIG. 3C is an example plot including vehicle region visualizations of the vehicle's interior that are used for implicit calibration of the user's predicted gaze, in accordance with some embodiments of the present disclosure.

Turning to FIG. 3C, FIG. 3C is an example plot including vehicle region visualizations of the vehicle's interior that are used for implicit calibration of the user's predicted gaze. The vehicle region visualizations correspond to one or more gaze saliency maps that indicate a user's most frequently viewed areas within a vehicle. The gaze saliency map 322 in FIG. 3B corresponds to region 338 in implicit gaze calibration region map 326. Based on the gaze saliency map 322, the boundaries of region 338 were determined and mapped to the interior of the vehicle. For example, the high density pattern of points 330 within region 338 correspond to region 324 of saliency map 322 indicate that the points with a high frequency of viewing by the user are clustered in a portion of the region 338. When the user gazes near region 338, implicit calibration may be performed to determine whether a predicted gaze location is within the boundaries of region 338. If the predicted gaze location falls outside of the boundaries but remains near the region 338, the calibration function(s) associated with the user may be modified using calculated offsets.

In some embodiments, the updated sensor data 106 may be applied to one or more DNNs 108 that are trained to compute various different outputs 110. Prior to application or input to the DNN(s) 108, the updated sensor data 106 may undergo pre-processing, such as to convert, crop, upscale, downscale, zoom in, rotate, and/or otherwise modify the updated sensor data 106. For example, where the updated sensor data 106 corresponds to camera image data, the image data may be cropped, downscaled, upscaled, flipped, rotated, and/or otherwise adjusted to a suitable input format for the respective DNN(s) 108. In some embodiments, the updated sensor data 106 may include image data representing an image(s), image data representing a video (e.g., snapshots of video), and/or sensor data representing representations of sensory fields of sensors (e.g., depth maps for LIDAR sensors, a value graph for ultrasonic sensors, etc.). In some examples, the updated sensor data 106 may be used without any pre-processing (e.g., in a raw or captured format), while in other examples, the updated sensor data 106 may undergo pre-processing (e.g., noise balancing, demosaicing, scaling, cropping, augmentation, white balancing, tone curve adjustment, etc., such as using a sensor data pre-processor (not shown)).

Although examples are described herein with respect to using the DNN(s) 108 (and/or to using DNNs, computer vision algorithms, image processing algorithms, machine learning models, etc., with respect to the user identifier 116, the facial landmark detector 122, the gaze origin determiner 124, and/or the gaze determiner 114), this is not intended to be limiting. For example and without limitation, the DNN(s) 108 and/or the computer vision algorithms, image processing algorithms, machine learning models, etc. described herein with respect to the user identifier 116, the facial landmark detector 122, the gaze origin determiner 124, and/or the gaze determiner 114, may include any type of machine learning model or algorithm, such as a machine learning model(s) using linear regression, logistic regression, decision trees, support vector machines (SVM), Naïve Bayes, k-nearest neighbor (Knn), K means clustering, random forest, dimensionality reduction algorithms, gradient boosting algorithms, neural networks (e.g., auto-encoders, convolutional, recurrent, perceptrons, long/short term memory/LS™, Hopfield, Boltzmann, deep belief, deconvolutional, generative adversarial, liquid state machine, etc.), areas of interest detection algorithms, computer vision algorithms, and/or other types of algorithms or machine learning models.

As an example, the DNN(s) 108 may process the updated sensor data 106 to generate facial features, facial landmarks, gaze origin, gaze locations, gaze vectors, angular offset, and/or other gaze information. For example, the detections may correspond to locations (e.g., in 2D image space, in 3D space, etc.), geometry, pose, semantic information, and/or other information about the detection. As such, for gaze information, eye measurements (e.g., angular offset between visual and optical axes of an eyeball, cornea radius and curvature, distance between pupil center and corneal center, refraction of aqueous humor and cornea) may be detected or calculated by a DNN(s) 108 processing the updated sensor data 106.

The outputs 110 of the DNN(s) 108 may undergo post-processing, in embodiments, such as by converting raw outputs to useful outputs—e.g., where a raw output corresponds to a confidences for each point or pixel that the point or pixel corresponds to a gaze location of a user, post-processing (e.g., filtering, clustering, etc.) may be executed to determine a final point(s) that corresponds to the gaze location of the user. This post-processing may include temporal filtering, weighting, outlier removal (e.g., removing pixels or points determined to be outliers), upscaling (e.g., the outputs may be predicted at a lower resolution than an input sensor data instance, and the output may be upscaled back to the input resolution), downscaling, curve fitting, and/or other post-processing techniques. The outputs 110—after post-processing, in embodiments—may be in either a 2D coordinate space (e.g., image space, etc.) and/or may be in a 3D coordinate system (e.g., a 3D coordinate system of the vehicle, as defined using vehicle geometry 120, for example).

The output(s) 110 of the DNN(s) 108 may include the gaze vectors, angular offsets, values in the three-dimensional world coordinate system of the vehicle, and/or other output types. In some embodiments, the output(s) 110 may include gaze vectors. The gaze vectors may include a magnitude and direction representative of the user's gaze toward a location within the interior of the vehicle. In some embodiments, the gaze vectors may be associated with a gaze origin, a point from which the gaze vector is projected in order to determine a predicted gaze location. In some embodiments, the output(s) 110 may include angular offsets. The angular offsets may represent an offset in angle between two axes with respect to a user (e.g., angle difference between visual and optical axes of the user). In some embodiments, the output(s) 110 may include three-dimensional coordinates. For instance, the output(s) 110 may include a predicted gaze location within a three-dimensional world coordinate system in the vehicle. In some embodiments, the output(s) 110 may include a predicted gaze location within a three-dimensional coordinate system from the perspective of a sensor (e.g., camera). The output(s) 110 may also include other information such as confidence levels with respect to calculated gaze predictions.

The calibrator 112 may calibrate or adjust output(s) 110 by using calibration functions associated with an identified user. For instance, calibrator 112 may operate on output(s) 110 using calibration functions retrieved by calibration functions selector 118 to produce an updated set of gaze prediction values used to compute a final gaze prediction value(s). In some embodiments, the calibrator 112 may verify the region or location of the user's predicted gaze to determine which calibration function to apply. For example, if the user is predicted to be gazing near a side-view mirror, the calibrator 112 may select only those calibration functions that are associated with the side-view mirror region and/or activated for use by a user with respect to a particular region. With the selected calibration function(s), the calibrator 112 may operate on output(s) 110 to produce updated gaze prediction values, which are, in turn, used to determine a final gaze prediction (e.g., predicted gaze location). In some embodiments, the updated gaze prediction values may be points (e.g., gaze locations) in a three-dimensional world coordinate system in the vehicle.

The facial landmark detector 122 may detect facial landmarks or features within the sensor data 102 and/or the updated sensor data 106. For instance, the facial landmark detector 122 may detect facial features such as eyes, eyebrows, nose, mouth, jawline, and/or the like, to aid in determining gaze predictions for a user. In some embodiments, the facial landmark detector may label each facial landmark by type (e.g., eyes, eyebrows, nose, mouth, jawline) and/or orientation (left or right side of the face). In scenarios where the updated sensor data 106 includes image data, the facial landmark detector 122 may also identify pixels associated with each facial landmark and/or generate labels corresponding thereto.

The gaze origin determiner 124 may use identified facial landmarks to determine a gaze origin. In some embodiments, the gaze origin determiner 124 may be used to determine a point at which a gaze vector may projected from in order to determine a predicted gaze location or direction. For instance, the gaze origin determiner 124 may use eyes and/or eyebrows identified by facial landmark detector 122 to determine that a gaze origin lies in between the user's eyes. The gaze origin determiner 124 may likewise use other facial landmarks to determine the gaze origin (e.g., a point at which a gaze vector begins). In some embodiments, the gaze origin determiner 124 may produce three-dimensional coordinates within a three-dimensional world coordinate system associated with an interior of a vehicle. Similarly, the gaze origin determiner 124 may produce three-dimensional coordinates within a three-dimensional coordinate system from the perspective of a sensor.

The gaze determiner 114 may use vehicle geometry 120 and a gaze origin, as calculated by gaze origin determiner 124, to determine a user's predicted gaze location or direction. For instance, the gaze determiner 114 may use gaze predictions about the user to determine a three-dimensional location within a vehicle's interior at which the user is gazing. In some embodiments, the gaze determiner 114 may place a gaze vector, as adjusted by calibrator 112, at a gaze origin, as calculated by gaze origin determiner 124, to determine a location that a user is gazing at. For example, once a gaze vector is placed as projecting from a gaze origin, an end of the gaze vector (e.g., where the gaze vector includes a depth value or extent value) and/or an intersection of the gaze vector with a surface of the vehicle 600 may provide a gaze location. As such, in embodiments, the gaze vector, as placed at the gaze origin, may be extended until it intersects with a point on the interior of the vehicle, producing a location within the vehicle interior that a user is gazing. Based on the predicted gaze location for a user determined by gaze determiner 114, responsive action may be taken by the vehicle such as alerting a driver to inattentiveness while driving or adjusting the position of the vehicle to prevent a driver from falling asleep at the wheel while driving.

In order to determine gaze location, the gaze origin calculated by gaze origin determiner 124 and updated values provided by calibrator 112 may be computed in—or converted to—a same coordinate system. For example, the gaze origin and updated values may be determined relative to a shared (e.g., world-space) coordinate system—e.g., with an origin at a location on the vehicle 600, such as on a point between the two front seats, etc. As such, where the updated values are computed in 2D image space, 3D space relative to a different origin, and/or otherwise in a 2D or 3D coordinate space that is not the shared coordinate space used by the gaze origin determiner 124 (e.g., 3D coordinate space from the perspective of a sensor embedded within the interior of the vehicle), the updated values may be converted to the shared coordinate space.

The vehicle geometry 120 may include information regarding the interior of a vehicle. For instance, the vehicle geometry may include a three-dimensional coordinate system that is mapped to the interior of the vehicle and may be used to determine a predicted gaze location. For example, the gaze determiner 114 may determine a predicted gaze location for a user and the vehicle geometry 120 may be used to determine which part of the interior of the vehicle the predicted gaze location is associated with. In some embodiments, the vehicle geometry 120 may have regions or areas within the interior of the vehicle labeled to illustrate which points surrounding a region within the interior are associated with a specific location (e.g., denote which coordinates are associated with the region surrounding a rear-view mirror).

In some embodiments, such as where the output 110 of the DNN(s) 108 is a three-dimensional location within the vehicle 600, the gaze origin determiner 124 and/or the vehicle geometry 120 may not be included within the process 100. For example, the gaze origin determiner 124 and/or the vehicle geometry 120 may be used by the gaze determiner to identify a three-dimensional location within the vehicle 600 using alternative output types—such as a gaze vector or an angular offset—but may not be required when the output 110 is the three-dimensional location.

Figure 1B:
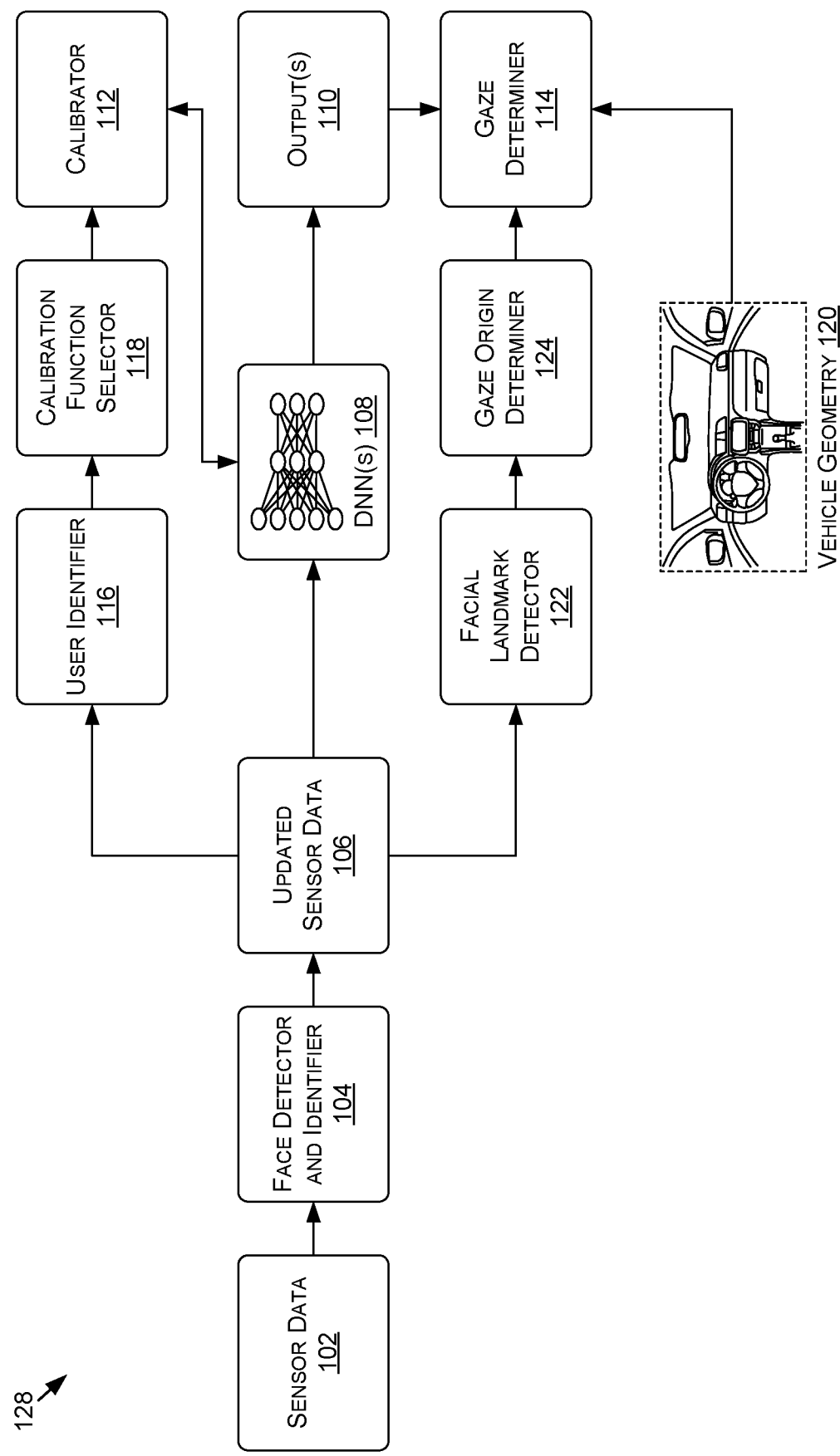
FIG. 1B is a data flow diagram illustrating an example process for applying personalized calibration functions to values from one or more last layers of a machine learning model, in accordance with some embodiments of the present disclosure.

With reference to FIG. 1B, FIG. 1B is a data flow diagram illustrating an example process 128 for applying personalized calibration functions to values from one or more last layers of a machine learning model, in accordance with some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory.

Similar to FIG. 1A, FIG. 1B includes components such as sensor data 102, face detector and identifier 104, updated sensor data 106, DNN(s) 108, output(s) 110, user identifier 116, calibration function selector 118, calibrator 112, facial landmark detector 122, gaze origin determiner 124, gaze determiner 114, and vehicle geometry 120, as described herein. As shown in FIG. 1B, several components in process 128 interact in a different manner when compared to process 100 in FIG. 1A. For instance, the calibrator 112 applies calibration functions, which are retrieved by calibration function selector 118, to one or more last layers of DNN(s) 108. In this way, calibrator 112 applies one or more calibration functions to operate on values represented by one or more (e.g., last) layers of DNN(s) 108. The interaction between calibrator 112 and DNN(s) 108 may be iterative (as illustrated by a double-sided arrow between calibrator 112 and DNN(s) 108) and the calibrator 112 may operate on one or more values computed using DNN(s) 108 until output(s) 110 are generated. By applying calibration functions to one or more values identified by DNN(s) 108 (versus output(s)

110), the calibration functions may operate on a large number of features versus a finite number of values in output(s) 110 and thus produce more accurate gaze information by which to estimate a predicted gaze location (e.g., final gaze prediction). In some embodiments, the calibration function may be used to updated the values stored in a layer(s) of the DNN(s) 108 such that the outputs 110 computed using the DNN(s) 108—e.g., a three-dimensional location within the vehicle, a gaze vector, an angular offset, etc.—may be used directly (e.g., may include inherent calibration) without requiring calibration as a post-process.

As such, with the calibration functions applied by calibrator 112 directly to the layer(s) of the DNN(s) 108, the output(s) 110 include the benefit of the calibration without additional processing from the generated calibration functions. Accordingly, as shown in FIG. 1B, gaze determiner 114 receives and operates on output(s) 110 versus updated values from calibrator 112 to determine a predicted gaze location or direction for a particular user. The process by which gaze determiner 114 operates on output(s) 110 is similar to that described herein with respect to updated values from calibrator 112 in FIG. 1A.

Figure 4:
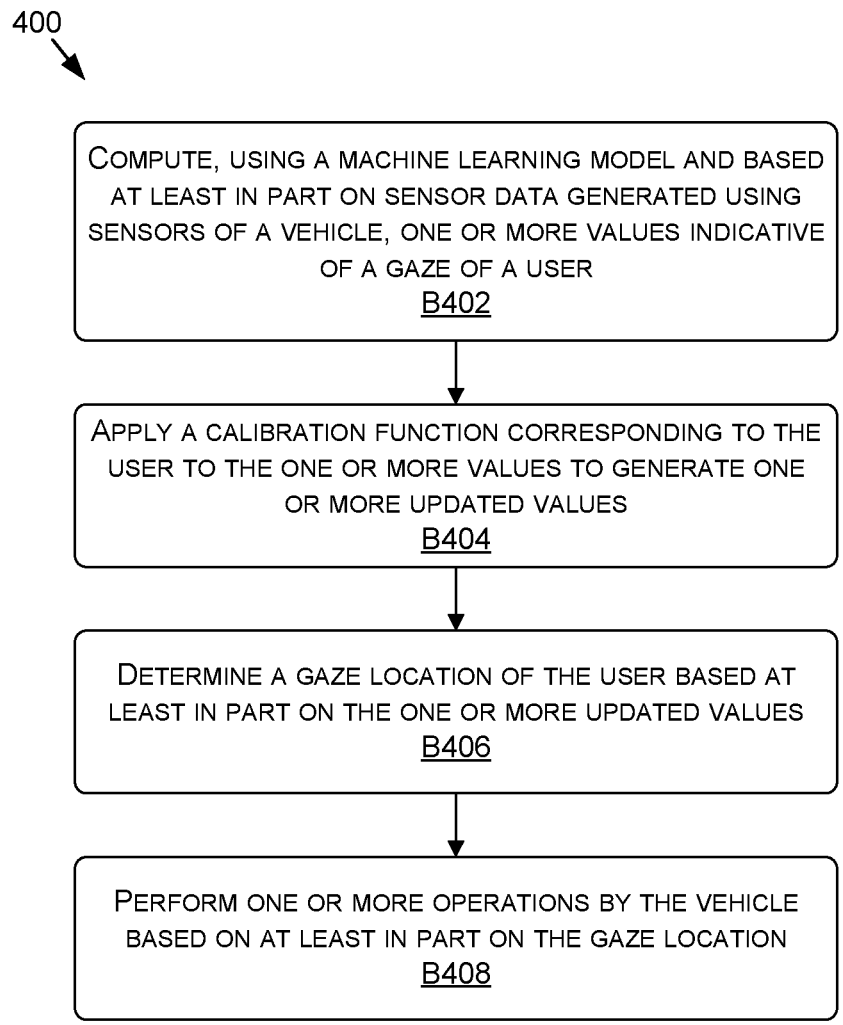
FIG. 4 is a flow diagram showing a method for applying a calibration function(s) to values indicative of a user's predicted gaze to determine a gaze location and perform a responsive operation(s), in accordance with some embodiments of the present disclosure.
Figure 5:
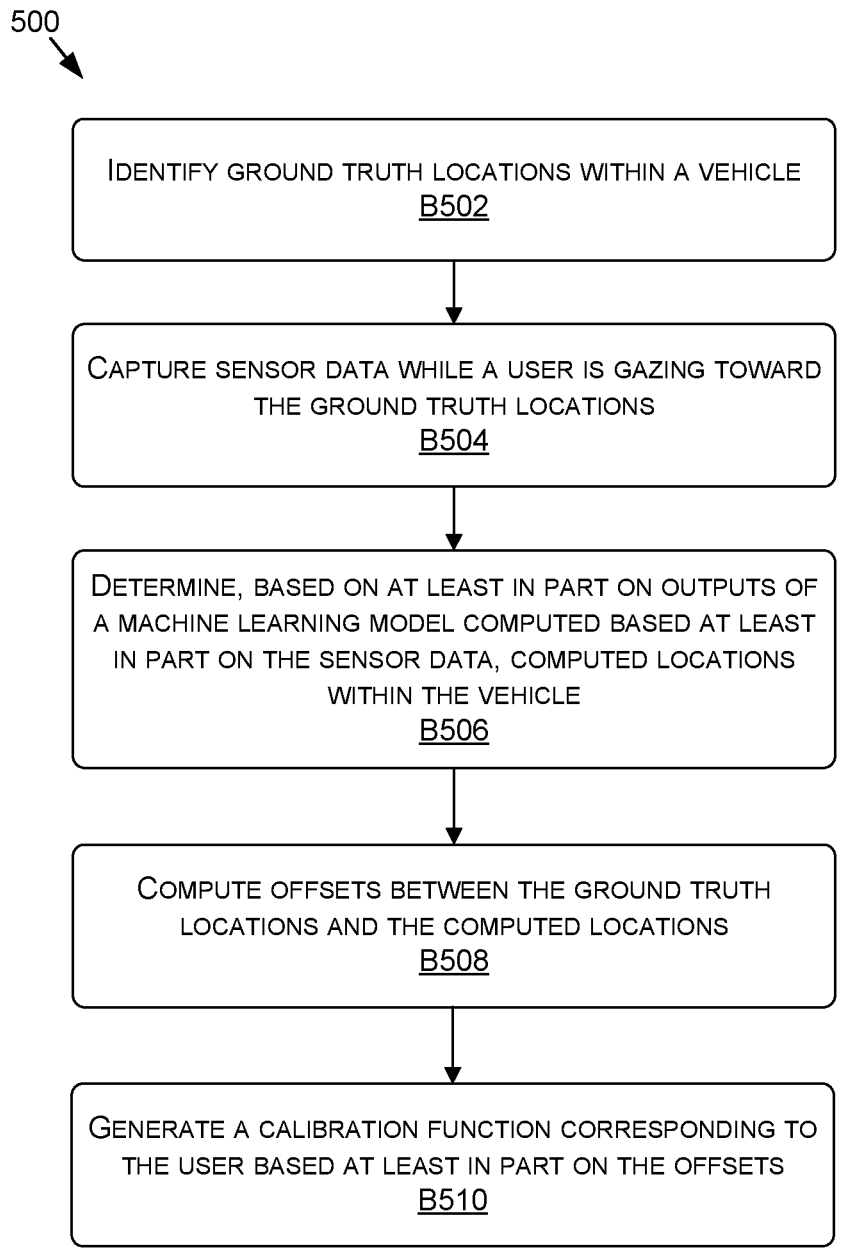
FIG. 5 is a flow diagram showing a method for generating a calibration function(s) based on offsets computed using a ground truth location(s) within a vehicle, in accordance with some embodiments of the present disclosure.

Now referring to FIGS. 4 and 5, each block of methods 400 and 500, described herein, comprises a computing process that may be performed using any combination of hardware, firmware, and/or software. For instance, various functions may be carried out by a processor executing instructions stored in memory. The methods 400 and 500 may also be embodied as computer-usable instructions stored on computer storage media. The methods 400 and 500 may be provided by a standalone application, a service or hosted service (standalone or in combination with another hosted service), or a plug-in to another product, to name a few. In addition, methods 400 and 500 are described, by way of example, with respect to the processes 100 and 128 of FIGS. 1A and 1B. However, these methods may additionally or alternatively be executed by any one system, or any combination of systems, including, but not limited to, those described herein.

FIG. 4 is a flow diagram showing a method 400 for applying calibration function(s) to values indicative of a user's gaze to determine a user's gaze location and perform operation(s), in accordance with some embodiments of the present disclosure. The method 400, at block B402, includes computing, using a machine learning model and based at least in part on sensor data generated using sensors of a vehicle, one or more values indicative of a gaze of a user. For example, FIGS. 2A and 2B provide examples of sensor data captured by one or more sensors within the vehicle 600 that may be used to compute one or more values representing the gaze of the user. In some embodiments, that sensor data 102 may be modified to produce updated sensor data 106. Using the updated sensor data 106, the machine learning model may produce output(s) 110. In some embodiments, the output(s) 110 from the machine learning model may be in the form of three-dimensional coordinates with respect to a three-dimensional world coordinate system associated with the interior of the vehicle 600, a gaze vector, an angular offset, and/or other gaze information, all of which are indicative of the gaze of the user.

The method 400, at block B404, includes applying a calibration function corresponding to the user to the one or more values to generate one or more updated values. For instance, a user may be identified from sensor data 102 and/or updated sensor data 106 and one or more calibration functions associated with the user may be retrieved. In some embodiments, the calibration functions may also be selected on the basis of a region that a user is predicted to be gazing at. For instance, if a user is predicted to be gazing at a rearview mirror, one or more calibration functions associated with the user and that region of the vehicle may be selected. In some embodiments, the calibration function(s) is applied to outputs of a machine learning model to generate one or more updated values. In some embodiments, the calibration function(s) may be applied to one or more layers of the machine learning model to produce updated values that may be used to generate output(s) from the machine learning model that incorporate adjustments by the calibration functions.

The method 400, at block B406, includes determining a gaze location of the user based at least in part on the one or more updated values. Based on the updated values, a gaze location, such as coordinates within a three-dimensional world coordinate system associated with the vehicle, may be determined. In some embodiments, a gaze origin may be calculated using facial landmark detection in order to determine a point from which a gaze vector may be projected from. Using the gaze vector projected from the gaze origin, a predicted gaze location within the interior of the vehicle may be determined.

The method 400, at block B408, includes performing one or more operations by the vehicle based on at least in part on the predicted gaze location. For example, if the predicted gaze location is determined to be the floor of the vehicle over a period of time, a determination that the user is falling asleep at the wheel may be determined. Based on this analysis, the vehicle may pull over and/or provide auditory and visual alerts to the user. Similarly, the predicted gaze locations over a period of time may indicate that a user has not viewed a road hazard in time to avoid it, causing the vehicle to maneuver around the road hazard.

FIG. 5 is a flow diagram showing a method 500 for generating calibration function(s) based on offsets computed using ground truth location(s) within a vehicle, in accordance with some embodiments of the present disclosure. The method 500, at block B502, includes identifying ground truth locations within a vehicle. For instance, locations within a vehicle that are frequently viewed by most users (e.g., side-view mirror, rear-view mirror, portion of the windshield directly in front of the user) may be used to determine ground truth locations. For example, FIG. 3A is an example of ten points, including a sensor (e.g., camera) capturing sensor data, that have been selected across the interior of the vehicle. In some embodiments, the ground truth locations may be selected to span the interior of the vehicle from left to right and/or top to bottom.

The method 500, at block B504, includes capturing sensor data while a user is gazing toward the ground truth locations. For instance, a user may be instructed (e.g., via auditory, visual, and/or haptic alerts) to gaze at each designated ground truth location while sensor data is captured.

The method 500, at block B506, includes determining, based on at least in part on outputs of a machine learning model computed based at least in part on the sensor data, computed locations within the vehicle. For instance, sensor data captured while a user was gazing at ground truth locations may be input into a machine learning model to determine a gaze prediction. For example, an image of a user gazing during an instruction to look at a rear-view mirror may be analyzed to provide an output such as a gaze prediction. In some embodiments, the gaze prediction may be converted into coordinates within a three-dimensional coordinate system associated with the interior of the vehicle to provide computer locations within the vehicle.

The method 500, at block B508, includes computing offsets between the ground truth locations and the computed locations. For instance, the computed locations may be several centimeters or inches away from the ground truth locations, as determined within a three-dimensional world coordinate system associated with the vehicle. An offset between the coordinates of each computed location and each ground truth location (and associated data) may be computed. In some embodiments, the offset may be calculated between other types of gaze information such as gaze vectors or angular offsets.

The method 500, at block B510, includes generating a calibration function corresponding to the user based at least in part on the offsets. For instance, based on the calculated offsets, one or more calibration functions may be generated. In some embodiments, the calibration function is specific to a user as well as a region of the vehicle (e.g., gaze predictions that fall within an area surrounding a rear-view mirror). Once generated through an explicit calibration method, the calibration function may be continually modified using implicit calibration methods, as described herein. Additionally, the calibration functions may then be used to adjust or refine outputs from the machine learning model and/or operate on features from one or more last layers of the machine learning model as described herein.

Example Autonomous Vehicle

Figure 6A:
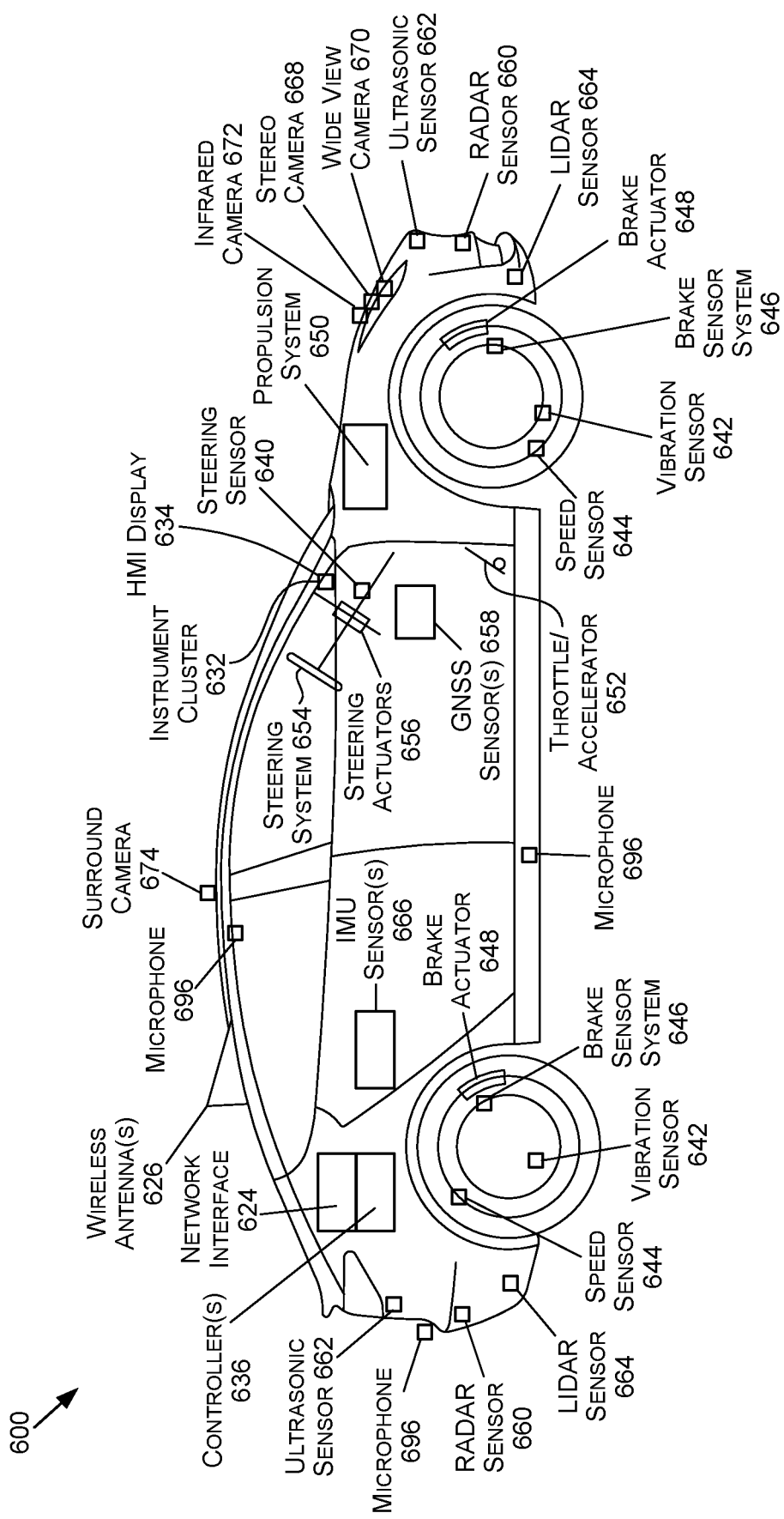
FIG. 6A is an illustration of an example autonomous vehicle, in accordance with some embodiments of the present disclosure.

FIG. 6A is an illustration of an example autonomous vehicle 600, in accordance with some embodiments of the present disclosure. The autonomous vehicle 600 (alternatively referred to herein as the "vehicle 600") may include, without limitation, a passenger vehicle, such as a car, a truck, a bus, a first responder vehicle, a shuttle, an electric or motorized bicycle, a motorcycle, a fire truck, a police vehicle, an ambulance, a boat, a construction vehicle, an underwater craft, a drone, and/or another type of vehicle (e.g., that is unmanned and/or that accommodates one or more passengers). Autonomous vehicles are generally described in terms of automation levels, defined by the National Highway Traffic Safety Administration (NHTSA), a division of the US Department of Transportation, and the Society of Automotive Engineers (SAE) "Taxonomy and Definitions for Terms Related to Driving Automation Systems for On-Road Motor Vehicles" (Standard No. J3016-201806, published on Jun. 15, 2018, Standard No. J3016-201609, published on Sep. 30, 2016, and previous and future versions of this standard). The vehicle 600 may be capable of functionality in accordance with one or more of Level 3-Level 5 of the autonomous driving levels. For example, the vehicle 600 may be capable of conditional automation (Level 3), high automation (Level 4), and/or full automation (Level 5), depending on the embodiment.

The vehicle 600 may include components such as a chassis, a vehicle body, wheels (e.g., 2, 4, 6, 8, 18, etc.), tires, axles, and other components of a vehicle. The vehicle 600 may include a propulsion system 650, such as an internal combustion engine, hybrid electric power plant, an all-electric engine, and/or another propulsion system type. The propulsion system 650 may be connected to a drive train of the vehicle 600, which may include a transmission, to enable the propulsion of the vehicle 600. The propulsion system 650 may be controlled in response to receiving signals from the throttle/accelerator 652.

A steering system 654, which may include a steering wheel, may be used to steer the vehicle 600 (e.g., along a desired path or route) when the propulsion system 650 is operating (e.g., when the vehicle is in motion). The steering system 654 may receive signals from a steering actuator 656. The steering wheel may be optional for full automation (Level 5) functionality.

The brake sensor system 646 may be used to operate the vehicle brakes in response to receiving signals from the brake actuators 648 and/or brake sensors.

Controller(s) 636, which may include one or more system on chips (SoCs) 604 (FIG. 6C) and/or GPU(s), may provide signals (e.g., representative of commands) to one or more components and/or systems of the vehicle 600. For example, the controller(s) may send signals to operate the vehicle brakes via one or more brake actuators 648, to operate the steering system 654 via one or more steering actuators 656, to operate the propulsion system 650 via one or more throttle/accelerators 652. The controller(s) 636 may include one or more onboard (e.g., integrated) computing devices (e.g., supercomputers) that process sensor signals, and output operation commands (e.g., signals representing commands) to enable autonomous driving and/or to assist a human driver in driving the vehicle 600. The controller(s) 636 may include a first controller 636 for autonomous driving functions, a second controller 636 for functional safety functions, a third controller 636 for artificial intelligence functionality (e.g., computer vision), a fourth controller 636 for infotainment functionality, a fifth controller 636 for redundancy in emergency conditions, and/or other controllers. In some examples, a single controller 636 may handle two or more of the above functionalities, two or more controllers 636 may handle a single functionality, and/or any combination thereof.

The controller(s) 636 may provide the signals for controlling one or more components and/or systems of the vehicle 600 in response to sensor data received from one or more sensors (e.g., sensor inputs). The sensor data may be received from, for example and without limitation, global navigation satellite systems sensor(s) 658 (e.g., Global Positioning System sensor(s)), RADAR sensor(s) 660, ultrasonic sensor(s) 662, LIDAR sensor(s) 664, inertial measurement unit (IMU) sensor(s) 666 (e.g., accelerometer(s), gyroscope(s), magnetic compass(es), magnetometer(s), etc.), microphone(s) 696, stereo camera(s) 668, wide-view camera(s) 670 (e.g., fisheye cameras), infrared camera(s) 672, surround camera(s) 674 (e.g., 360 degree cameras), long-range and/or mid-range camera(s) 698, speed sensor(s) 644 (e.g., for measuring the speed of the vehicle 600), vibration sensor(s) 642, steering sensor(s) 640, brake sensor(s) (e.g., as part of the brake sensor system 646), and/or other sensor types.

One or more of the controller(s) 636 may receive inputs (e.g., represented by input data) from an instrument cluster 632 of the vehicle 600 and provide outputs (e.g., represented by output data, display data, etc.) via a human-machine interface (HMI) display 634, an audible annunciator, a loudspeaker, and/or via other components of the vehicle 600. The outputs may include information such as vehicle velocity, speed, time, map data (e.g., the HD map 622 of FIG. 6C), location data (e.g., the vehicle's 600 location, such as on a map), direction, location of other vehicles (e.g., an occupancy grid), information about objects and status of objects as perceived by the controller(s) 636, etc. For example, the HMI display 634 may display information about the presence of one or more objects (e.g., a street sign, caution sign, traffic light changing, etc.), and/or information about driving maneuvers the vehicle has made, is making, or will make (e.g., changing lanes now, taking exit 34B in two miles, etc.).

The vehicle 600 further includes a network interface 624 which may use one or more wireless antenna(s) 626 and/or modem(s) to communicate over one or more networks. For example, the network interface 624 may be capable of communication over LTE, WCDMA, UMTS, GSM, CDMA2000, etc. The wireless antenna(s) 626 may also enable communication between objects in the environment (e.g., vehicles, mobile devices, etc.), using local area network(s), such as Bluetooth, Bluetooth LE, Z-Wave, ZigBee, etc., and/or low power wide-area network(s) (LPWANs), such as LoRaWAN, SigFox, etc.

Figure 6B:
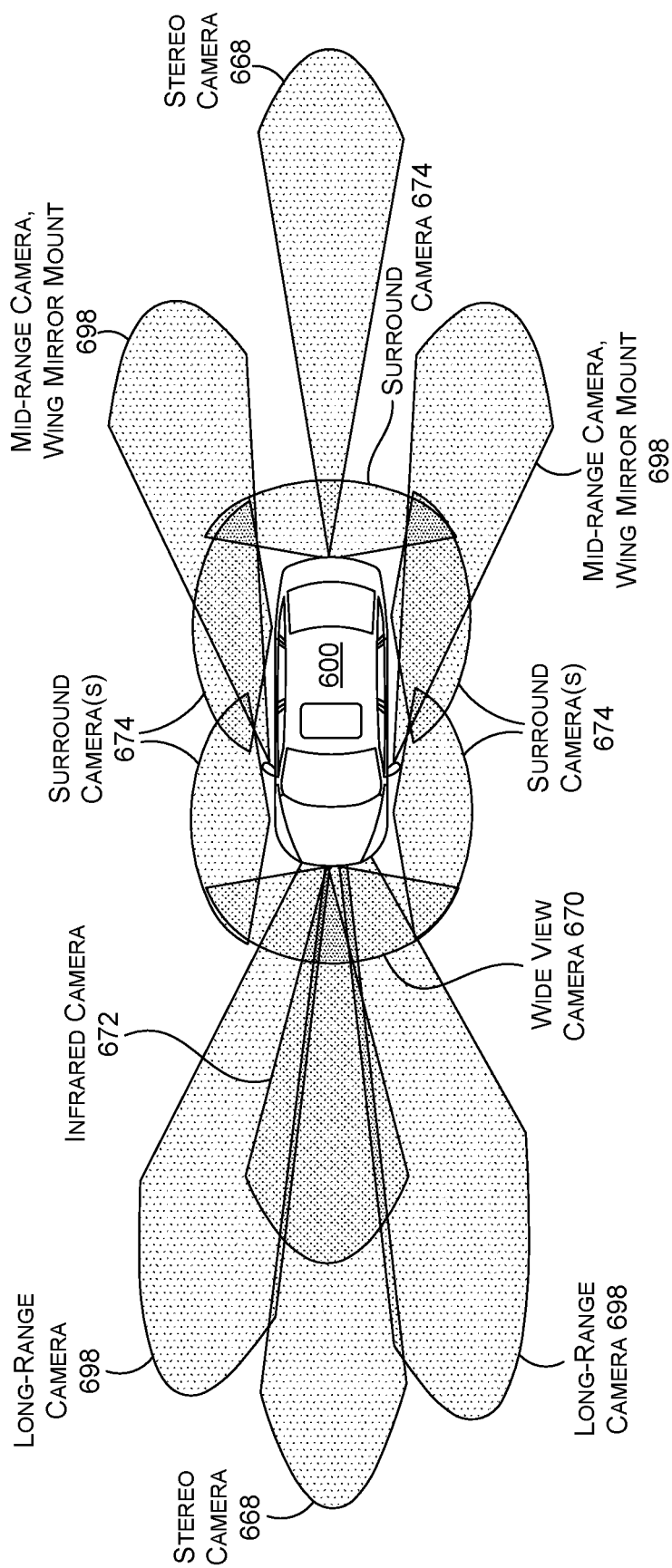
FIG. 6B is an example of camera locations and fields of view for the example autonomous vehicle of FIG. 6A, in accordance with some embodiments of the present disclosure.

FIG. 6B is an example of camera locations and fields of view for the example autonomous vehicle 600 of FIG. 6A, in accordance with some embodiments of the present disclosure. The cameras and respective fields of view are one example embodiment and are not intended to be limiting. For example, additional and/or alternative cameras may be included and/or the cameras may be located at different locations on the vehicle 600.

The camera types for the cameras may include, but are not limited to, digital cameras that may be adapted for use with the components and/or systems of the vehicle 600. The camera(s) may operate at automotive safety integrity level (ASIL) B and/or at another ASIL. The camera types may be capable of any image capture rate, such as 60 frames per second (fps), 120 fps, 240 fps, etc., depending on the embodiment. The cameras may be capable of using rolling shutters, global shutters, another type of shutter, or a combination thereof. In some examples, the color filter array may include a red clear clear clear (RCCC) color filter array, a red clear clear blue (RCCB) color filter array, a red blue green clear (RBGC) color filter array, a Foveon X3 color filter array, a Bayer sensors (RGGB) color filter array, a monochrome sensor color filter array, and/or another type of color filter array. In some embodiments, clear pixel cameras, such as cameras with an RCCC, an RCCB, and/or an RBGC color filter array, may be used in an effort to increase light sensitivity.

In some examples, one or more of the camera(s) may be used to perform advanced driver assistance systems (ADAS) functions (e.g., as part of a redundant or fail-safe design). For example, a Multi-Function Mono Camera may be installed to provide functions including lane departure warning, traffic sign assist and intelligent headlamp control. One or more of the camera(s) (e.g., all of the cameras) may record and provide image data (e.g., video) simultaneously.

One or more of the cameras may be mounted in a mounting assembly, such as a custom designed (3-D printed) assembly, in order to cut out stray light and reflections from within the car (e.g., reflections from the dashboard reflected in the windshield mirrors) which may interfere with the camera's image data capture abilities. With reference to wing-mirror mounting assemblies, the wing-mirror assemblies may be custom 3-D printed so that the camera mounting plate matches the shape of the wing-mirror. In some examples, the camera(s) may be integrated into the wing-mirror. For side-view cameras, the camera(s) may also be integrated within the four pillars at each corner of the cabin.

Cameras with a field of view that include portions of the environment in front of the vehicle 600 (e.g., front-facing cameras) may be used for surround view, to help identify forward facing paths and obstacles, as well aid in, with the help of one or more controllers 636 and/or control SoCs, providing information critical to generating an occupancy grid and/or determining the preferred vehicle paths. Front-facing cameras may be used to perform many of the same ADAS functions as LIDAR, including emergency braking, pedestrian detection, and collision avoidance. Front-facing cameras may also be used for ADAS functions and systems including Lane Departure Warnings ("LDW"), Autonomous Cruise Control ("ACC"), and/or other functions such as traffic sign recognition.

A variety of cameras may be used in a front-facing configuration, including, for example, a monocular camera platform that includes a CMOS (complementary metal oxide semiconductor) color imager. Another example may be a wide-view camera(s) 670 that may be used to perceive objects coming into view from the periphery (e.g., pedestrians, crossing traffic or bicycles). Although only one wide-view camera is illustrated in FIG. 6B, there may any number of wide-view cameras 670 on the vehicle 600. In addition, long-range camera(s) 698 (e.g., a long-view stereo camera pair) may be used for depth-based object detection, especially for objects for which a neural network has not yet been trained. The long-range camera(s) 698 may also be used for object detection and classification, as well as basic object tracking.

One or more stereo cameras 668 may also be included in a front-facing configuration. The stereo camera(s) 668 may include an integrated control unit comprising a scalable processing unit, which may provide a programmable logic (FPGA) and a multi-core micro-processor with an integrated CAN or Ethernet interface on a single chip. Such a unit may be used to generate a 3-D map of the vehicle's environment, including a distance estimate for all the points in the image. An alternative stereo camera(s) 668 may include a compact stereo vision sensor(s) that may include two camera lenses (one each on the left and right) and an image processing chip that may measure the distance from the vehicle to the target object and use the generated information (e.g., metadata) to activate the autonomous emergency braking and lane departure warning functions. Other types of stereo camera(s) 668 may be used in addition to, or alternatively from, those described herein.

Cameras with a field of view that include portions of the environment to the side of the vehicle 600 (e.g., side-view cameras) may be used for surround view, providing information used to create and update the occupancy grid, as well as to generate side impact collision warnings. For example, surround camera(s) 674 (e.g., four surround cameras 674 as illustrated in FIG. 6B) may be positioned to on the vehicle 600. The surround camera(s) 674 may include wide-view camera(s) 670, fisheye camera(s), 360 degree camera(s), and/or the like. Four example, four fisheye cameras may be positioned on the vehicle's front, rear, and sides. In an alternative arrangement, the vehicle may use three surround camera(s) 674 (e.g., left, right, and rear), and may leverage one or more other camera(s) (e.g., a forward-facing camera) as a fourth surround view camera.

Cameras with a field of view that include portions of the environment to the rear of the vehicle 600 (e.g., rear-view cameras) may be used for park assistance, surround view, rear collision warnings, and creating and updating the occupancy grid. A wide variety of cameras may be used including, but not limited to, cameras that are also suitable as a front-facing camera(s) (e.g., long-range and/or mid-range camera(s) 698, stereo camera(s) 668), infrared camera(s) 672, etc.), as described herein.

Figure 6C:
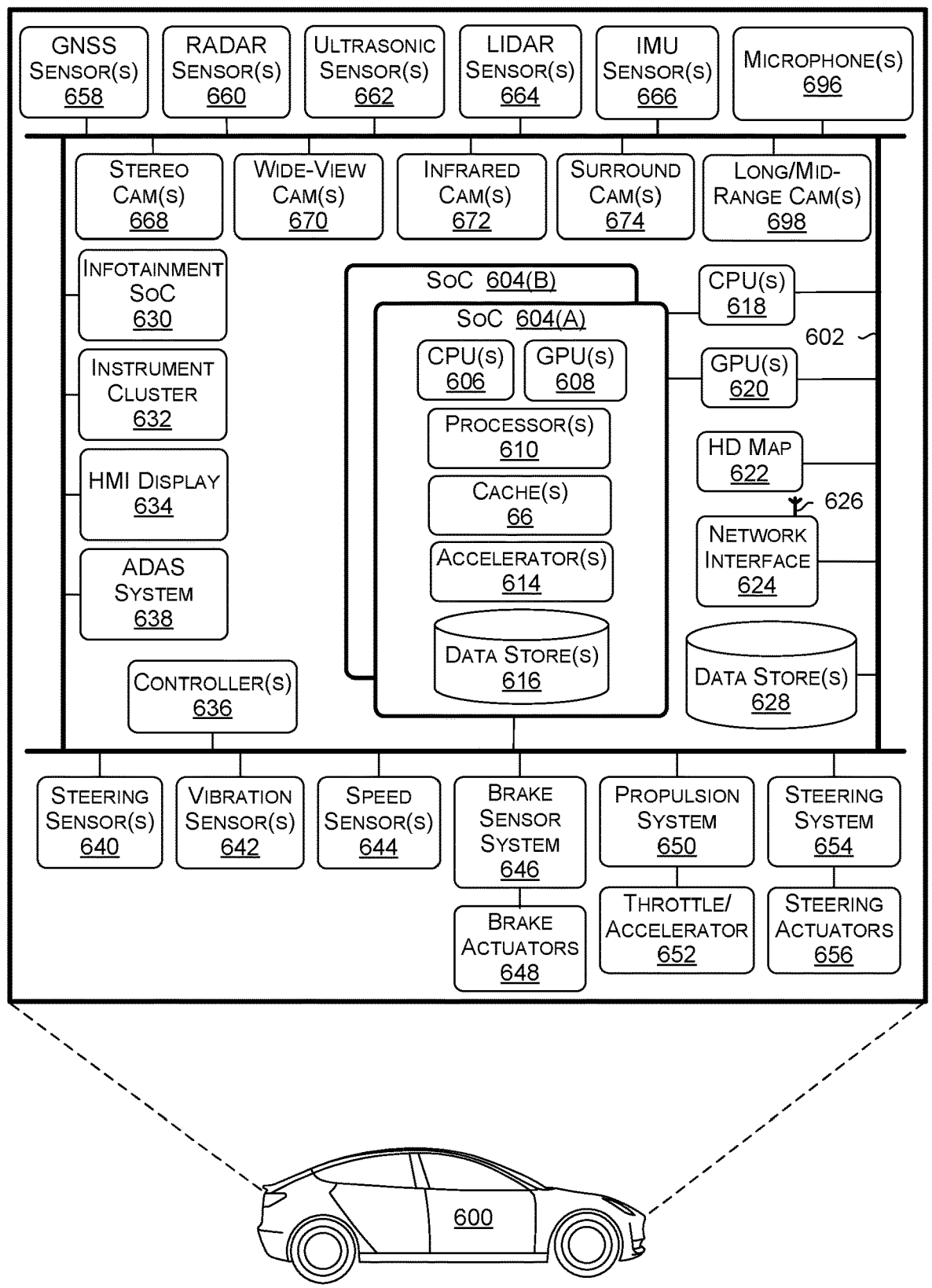
FIG. 6C is a block diagram of an example system architecture for the example autonomous vehicle of FIG. 6A, in accordance with some embodiments of the present disclosure.

FIG. 6C is a block diagram of an example system architecture for the example autonomous vehicle 600 of FIG. 6A, in accordance with some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory.

Each of the components, features, and systems of the vehicle 600 in FIG. 6C are illustrated as being connected via bus 602. The bus 602 may include a Controller Area Network (CAN) data interface (alternatively referred to herein as a "CAN bus"). A CAN may be a network inside the vehicle 600 used to aid in control of various features and functionality of the vehicle 600, such as actuation of brakes, acceleration, braking, steering, windshield wipers, etc. A CAN bus may be configured to have dozens or even hundreds of nodes, each with its own unique identifier (e.g., a CAN ID). The CAN bus may be read to find steering wheel angle, ground speed, engine revolutions per minute (RPMs), button positions, and/or other vehicle status indicators. The CAN bus may be ASIL B compliant.

Although the bus 602 is described herein as being a CAN bus, this is not intended to be limiting. For example, in addition to, or alternatively from, the CAN bus, FlexRay and/or Ethernet may be used. Additionally, although a single line is used to represent the bus 602, this is not intended to be limiting. For example, there may be any number of busses 602, which may include one or more CAN busses, one or more FlexRay busses, one or more Ethernet busses, and/or one or more other types of busses using a different protocol. In some examples, two or more busses 602 may be used to perform different functions, and/or may be used for redundancy. For example, a first bus 602 may be used for collision avoidance functionality and a second bus 602 may be used for actuation control. In any example, each bus 602 may communicate with any of the components of the vehicle 600, and two or more busses 602 may communicate with the same components. In some examples, each SoC 604, each controller 636, and/or each computer within the vehicle may have access to the same input data (e.g., inputs from sensors of the vehicle 600), and may be connected to a common bus, such the CAN bus.

The vehicle 600 may include one or more controller(s) 636, such as those described herein with respect to FIG. 6A. The controller(s) 636 may be used for a variety of functions. The controller(s) 636 may be coupled to any of the various other components and systems of the vehicle 600, and may be used for control of the vehicle 600, artificial intelligence of the vehicle 600, infotainment for the vehicle 600, and/or the like.

The vehicle 600 may include a system(s) on a chip (SoC) 604. The SoC 604 may include CPU(s) 606, GPU(s) 608, processor(s) 610, cache(s) 612, accelerator(s) 614, data store(s) 616, and/or other components and features not illustrated. The SoC(s) 604 may be used to control the vehicle 600 in a variety of platforms and systems. For example, the SoC(s) 604 may be combined in a system (e.g., the system of the vehicle 600) with an HD map 622 which may obtain map refreshes and/or updates via a network interface 624 from one or more servers (e.g., server(s) 678 of FIG. 6D).

The CPU(s) 606 may include a CPU cluster or CPU complex (alternatively referred to herein as a "CCPLEX").

The CPU(s) 606 may include multiple cores and/or L2 caches. For example, in some embodiments, the CPU(s) 606 may include eight cores in a coherent multi-processor configuration. In some embodiments, the CPU(s) 606 may include four dual-core clusters where each cluster has a dedicated L2 cache (e.g., a 2 MB L2 cache). The CPU(s) 606 (e.g., the CCPLEX) may be configured to support simultaneous cluster operation enabling any combination of the clusters of the CPU(s) 606 to be active at any given time.

The CPU(s) 606 may implement power management capabilities that include one or more of the following features: individual hardware blocks may be clock-gated automatically when idle to save dynamic power; each core clock may be gated when the core is not actively executing instructions due to execution of WFI/WFE instructions; each core may be independently power-gated; each core cluster may be independently clock-gated when all cores are clock-gated or power-gated; and/or each core cluster may be independently power-gated when all cores are power-gated. The CPU(s) 606 may further implement an enhanced algorithm for managing power states, where allowed power states and expected wakeup times are specified, and the hardware/microcode determines the best power state to enter for the core, cluster, and CCPLEX. The processing cores may support simplified power state entry sequences in software with the work offloaded to microcode.

The GPU(s) 608 may include an integrated GPU (alternatively referred to herein as an "iGPU"). The GPU(s) 608 may be programmable and may be efficient for parallel workloads. The GPU(s) 608, in some examples, may use an enhanced tensor instruction set. The GPU(s) 608 may include one or more streaming microprocessors, where each streaming microprocessor may include an L1 cache (e.g., an L1 cache with at least 96 KB storage capacity), and two or more of the streaming microprocessors may share an L2 cache (e.g., an L2 cache with a 512 KB storage capacity). In some embodiments, the GPU(s) 608 may include at least eight streaming microprocessors. The GPU(s) 608 may use compute application programming interface(s) (API(s)). In addition, the GPU(s) 608 may use one or more parallel computing platforms and/or programming models (e.g., NVIDIA's CUDA).

The GPU(s) 608 may be power-optimized for best performance in automotive and embedded use cases. For example, the GPU(s) 608 may be fabricated on a Fin field-effect transistor (FinFET). However, this is not intended to be limiting and the GPU(s) 608 may be fabricated using other semiconductor manufacturing processes. Each streaming microprocessor may incorporate a number of mixed-precision processing cores partitioned into multiple blocks. For example, and without limitation, 64 PF32 cores and 32 PF64 cores may be partitioned into four processing blocks. In such an example, each processing block may be allocated 16 FP32 cores, 8 FP64 cores, 16 INT32 cores, two mixed-precision NVIDIA TENSOR COREs for deep learning matrix arithmetic, an L0 instruction cache, a warp scheduler, a dispatch unit, and/or a 64 KB register file. In addition, the streaming microprocessors may include independent parallel integer and floating-point data paths to provide for efficient execution of workloads with a mix of computation and addressing calculations. The streaming microprocessors may include independent thread scheduling capability to enable finer-grain synchronization and cooperation between parallel threads. The streaming microprocessors may include a combined L1 data cache and shared memory unit in order to improve performance while simplifying programming.

The GPU(s) 608 may include a high bandwidth memory (HBM) and/or a 16 GB HBM2 memory subsystem to provide, in some examples, about 900 GB/second peak memory bandwidth. In some examples, in addition to, or alternatively from, the HBM memory, a synchronous graphics random-access memory (SGRAM) may be used, such as a graphics double data rate type five synchronous random-access memory (GDDR5).

The GPU(s) 608 may include unified memory technology including access counters to allow for more accurate migration of memory pages to the processor that accesses them most frequently, thereby improving efficiency for memory ranges shared between processors. In some examples, address translation services (ATS) support may be used to allow the GPU(s) 608 to access the CPU(s) 606 page tables directly. In such examples, when the GPU(s) 608 memory management unit (MMU) experiences a miss, an address translation request may be transmitted to the CPU(s) 606. In response, the CPU(s) 606 may look in its page tables for the virtual-to-physical mapping for the address and transmits the translation back to the GPU(s) 608. As such, unified memory technology may allow a single unified virtual address space for memory of both the CPU(s) 606 and the GPU(s) 608, thereby simplifying the GPU(s) 608 programming and porting of applications to the GPU(s) 608.

In addition, the GPU(s) 608 may include an access counter that may keep track of the frequency of access of the GPU(s) 608 to memory of other processors. The access counter may help ensure that memory pages are moved to the physical memory of the processor that is accessing the pages most frequently.

The SoC(s) 604 may include any number of cache(s) 612, including those described herein. For example, the cache(s) 612 may include an L3 cache that is available to both the CPU(s) 606 and the GPU(s) 608 (e.g., that is connected both the CPU(s) 606 and the GPU(s) 608). The cache(s) 612 may include a write-back cache that may keep track of states of lines, such as by using a cache coherence protocol (e.g., MEI, MESI, MSI, etc.). The L3 cache may include 4 MB or more, depending on the embodiment, although smaller cache sizes may be used.

The SoC(s) 604 may include an arithmetic logic unit(s) (ALU(s)) which may be leveraged in performing processing with respect to any of the variety of tasks or operations of the vehicle 600—such as processing DNNs. In addition, the SoC(s) 604 may include a floating point unit(s) (FPU(s))—or other math coprocessor or numeric coprocessor types—for performing mathematical operations within the system. For example, the SoC(s) 104 may include one or more FPUs integrated as execution units within a CPU(s) 606 and/or GPU(s) 608.

The SoC(s) 604 may include one or more accelerators 614 (e.g., hardware accelerators, software accelerators, or a combination thereof). For example, the SoC(s) 604 may include a hardware acceleration cluster that may include optimized hardware accelerators and/or large on-chip memory. The large on-chip memory (e.g., 4 MB of SRAM), may enable the hardware acceleration cluster to accelerate neural networks and other calculations. The hardware acceleration cluster may be used to complement the GPU(s) 608 and to off-load some of the tasks of the GPU(s) 608 (e.g., to free up more cycles of the GPU(s) 608 for performing other tasks). As an example, the accelerator(s) 614 may be used for targeted workloads (e.g., perception, convolutional neural networks (CNNs), etc.) that are stable enough to be amenable to acceleration. The term "CNN," as used herein, may include all types of CNNs, including region-based or regional convolutional neural networks (RCNNs) and Fast RCNNs (e.g., as used for object detection).

The accelerator(s) 614 (e.g., the hardware acceleration cluster) may include a deep learning accelerator(s) (DLA). The DLA(s) may include one or more Tensor processing units (TPUs) that may be configured to provide an additional ten trillion operations per second for deep learning applications and inferencing. The TPUs may be accelerators configured to, and optimized for, performing image processing functions (e.g., for CNNs, RCNNs, etc.). The DLA(s) may further be optimized for a specific set of neural network types and floating point operations, as well as inferencing. The design of the DLA(s) may provide more performance per millimeter than a general-purpose GPU, and vastly exceeds the performance of a CPU. The TPU(s) may perform several functions, including a single-instance convolution function, supporting, for example, INT8, INT16, and FP16 data types for both features and weights, as well as post-processor functions.

The DLA(s) may quickly and efficiently execute neural networks, especially CNNs, on processed or unprocessed data for any of a variety of functions, including, for example and without limitation: a CNN for object identification and detection using data from camera sensors; a CNN for distance estimation using data from camera sensors; a CNN for emergency vehicle detection and identification and detection using data from microphones; a CNN for facial recognition and vehicle owner identification using data from camera sensors; and/or a CNN for security and/or safety related events.

The DLA(s) may perform any function of the GPU(s) 608, and by using an inference accelerator, for example, a designer may target either the DLA(s) or the GPU(s) 608 for any function. For example, the designer may focus processing of CNNs and floating point operations on the DLA(s) and leave other functions to the GPU(s) 608 and/or other accelerator(s) 614.

The accelerator(s) 614 (e.g., the hardware acceleration cluster) may include a programmable vision accelerator(s) (PVA), which may alternatively be referred to herein as a computer vision accelerator. The PVA(s) may be designed and configured to accelerate computer vision algorithms for the advanced driver assistance systems (ADAS), autonomous driving, and/or augmented reality (AR) and/or virtual reality (VR) applications. The PVA(s) may provide a balance between performance and flexibility. For example, each PVA(s) may include, for example and without limitation, any number of reduced instruction set computer (RISC) cores, direct memory access (DMA), and/or any number of vector processors.

The RISC cores may interact with image sensors (e.g., the image sensors of any of the cameras described herein), image signal processor(s), and/or the like. Each of the RISC cores may include any amount of memory. The RISC cores may use any of a number of protocols, depending on the embodiment. In some examples, the RISC cores may execute a real-time operating system (RTOS). The RISC cores may be implemented using one or more integrated circuit devices, application specific integrated circuits (ASICs), and/or memory devices. For example, the RISC cores may include an instruction cache and/or a tightly coupled RAM.

The DMA may enable components of the PVA(s) to access the system memory independently of the CPU(s) 606. The DMA may support any number of features used to provide optimization to the PVA including, but not limited to, supporting multi-dimensional addressing and/or circular addressing. In some examples, the DMA may support up to six or more dimensions of addressing, which may include block width, block height, block depth, horizontal block stepping, vertical block stepping, and/or depth stepping.

The vector processors may be programmable processors that may be designed to efficiently and flexibly execute programming for computer vision algorithms and provide signal processing capabilities. In some examples, the PVA may include a PVA core and two vector processing subsystem partitions. The PVA core may include a processor subsystem, DMA engine(s) (e.g., two DMA engines), and/or other peripherals. The vector processing subsystem may operate as the primary processing engine of the PVA, and may include a vector processing unit (VPU), an instruction cache, and/or vector memory (e.g., VMEM). A VPU core may include a digital signal processor such as, for example, a single instruction, multiple data (SIMD), very long instruction word (VLIW) digital signal processor. The combination of the SIMD and VLIW may enhance throughput and speed.

Each of the vector processors may include an instruction cache and may be coupled to dedicated memory. As a result, in some examples, each of the vector processors may be configured to execute independently of the other vector processors. In other examples, the vector processors that are included in a particular PVA may be configured to employ data parallelism. For example, in some embodiments, the plurality of vector processors included in a single PVA may execute the same computer vision algorithm, but on different regions of an image. In other examples, the vector processors included in a particular PVA may simultaneously execute different computer vision algorithms, on the same image, or even execute different algorithms on sequential images or portions of an image. Among other things, any number of PVAs may be included in the hardware acceleration cluster and any number of vector processors may be included in each of the PVAs. In addition, the PVA(s) may include additional error correcting code (ECC) memory, to enhance overall system safety.

The accelerator(s) 614 (e.g., the hardware acceleration cluster) may include a computer vision network on-chip and SRAM, for providing a high-bandwidth, low latency SRAM for the accelerator(s) 614. In some examples, the on-chip memory may include at least 4 MB SRAM, consisting of, for example and without limitation, eight field-configurable memory blocks, that may be accessible by both the PVA and the DLA. Each pair of memory blocks may include an advanced peripheral bus (APB) interface, configuration circuitry, a controller, and a multiplexer. Any type of memory may be used. The PVA and DLA may access the memory via a backbone that provides the PVA and DLA with high-speed access to memory. The backbone may include a computer vision network on-chip that interconnects the PVA and the DLA to the memory (e.g., using the APB).

The computer vision network on-chip may include an interface that determines, before transmission of any control signal/address/data, that both the PVA and the DLA provide ready and valid signals. Such an interface may provide for separate phases and separate channels for transmitting control signals/addresses/data, as well as burst-type communications for continuous data transfer. This type of interface may comply with ISO 26262 or IEC 61508 standards, although other standards and protocols may be used.

In some examples, the SoC(s) 604 may include a real-time ray-tracing hardware accelerator, such as described in U.S. patent application Ser. No. 16/101,232, filed on Aug. 10, 2018. The real-time ray-tracing hardware accelerator may be used to quickly and efficiently determine the positions and extents of objects (e.g., within a world model), to generate real-time visualization simulations, for RADAR signal interpretation, for sound propagation synthesis and/or analysis, for simulation of SONAR systems, for general wave propagation simulation, for comparison to LIDAR data for purposes of localization and/or other functions, and/or for other uses. In some embodiments, one or more tree traversal units (TTUs) may be used for executing one or more ray-tracing related operations.

The accelerator(s) 614 (e.g., the hardware accelerator cluster) have a wide array of uses for autonomous driving. The PVA may be a programmable vision accelerator that may be used for key processing stages in ADAS and autonomous vehicles. The PVA's capabilities are a good match for algorithmic domains needing predictable processing, at low power and low latency. In other words, the PVA performs well on semi-dense or dense regular computation, even on small data sets, which need predictable run-times with low latency and low power. Thus, in the context of platforms for autonomous vehicles, the PVAs are designed to run classic computer vision algorithms, as they are efficient at object detection and operating on integer math.

For example, according to one embodiment of the technology, the PVA is used to perform computer stereo vision. A semi-global matching-based algorithm may be used in some examples, although this is not intended to be limiting. Many applications for Level 3-5 autonomous driving require motion estimation/stereo matching on-the-fly (e.g., structure from motion, pedestrian recognition, lane detection, etc.). The PVA may perform computer stereo vision function on inputs from two monocular cameras.

In some examples, the PVA may be used to perform dense optical flow. According to process raw RADAR data (e.g., using a 4D Fast Fourier Transform) to provide Processed RADAR. In other examples, the PVA is used for time of flight depth processing, by processing raw time of flight data to provide processed time of flight data, for example.

The DLA may be used to run any type of network to enhance control and driving safety, including for example, a neural network that outputs a measure of confidence for each object detection. Such a confidence value may be interpreted as a probability, or as providing a relative "weight" of each detection compared to other detections. This confidence value enables the system to make further decisions regarding which detections should be considered as true positive detections rather than false positive detections. For example, the system may set a threshold value for the confidence and consider only the detections exceeding the threshold value as true positive detections. In an automatic emergency braking (AEB) system, false positive detections would cause the vehicle to automatically perform emergency braking, which is obviously undesirable. Therefore, only the most confident detections should be considered as triggers for AEB The DLA may run a neural network for regressing the confidence value. The neural network may take as its input at least some subset of parameters, such as bounding box dimensions, ground plane estimate obtained (e.g. from another subsystem), inertial measurement unit (IMU) sensor 666 output that correlates with the vehicle 600 orientation, distance, 3D location estimates of the object obtained from the neural network and/or other sensors (e.g., LIDAR sensor(s) 664 or RADAR sensor(s) 660), among others.

The SoC(s) 604 may include data store(s) 616 (e.g., memory). The data store(s) 616 may be on-chip memory of the SoC(s) 604, which may store neural networks to be executed on the GPU and/or the DLA. In some examples, the data store(s) 616 may be large enough in capacity to store multiple instances of neural networks for redundancy and safety. The data store(s) 612 may comprise L2 or L3 cache(s) 612. Reference to the data store(s) 616 may include reference to the memory associated with the PVA, DLA, and/or other accelerator(s) 614, as described herein.

The SoC(s) 604 may include one or more processor(s) 610 (e.g., embedded processors). The processor(s) 610 may include a boot and power management processor that may be a dedicated processor and subsystem to handle boot power and management functions and related security enforcement. The boot and power management processor may be a part of the SoC(s) 604 boot sequence and may provide runtime power management services. The boot power and management processor may provide clock and voltage programming, assistance in system low power state transitions, management of SoC(s) 604 thermals and temperature sensors, and/or management of the SoC(s) 604 power states. Each temperature sensor may be implemented as a ring-oscillator whose output frequency is proportional to temperature, and the SoC(s) 604 may use the ring-oscillators to detect temperatures of the CPU(s) 606, GPU(s) 608, and/or accelerator(s) 614. If temperatures are determined to exceed a threshold, the boot and power management processor may enter a temperature fault routine and put the SoC(s) 604 into a lower power state and/or put the vehicle 600 into a chauffeur to safe stop mode (e.g., bring the vehicle 600 to a safe stop).

The processor(s) 610 may further include a set of embedded processors that may serve as an audio processing engine. The audio processing engine may be an audio subsystem that enables full hardware support for multi-channel audio over multiple interfaces, and a broad and flexible range of audio I/O interfaces. In some examples, the audio processing engine is a dedicated processor core with a digital signal processor with dedicated RAM.

The processor(s) 610 may further include an always on processor engine that may provide necessary hardware features to support low power sensor management and wake use cases. The always on processor engine may include a processor core, a tightly coupled RAM, supporting peripherals (e.g., timers and interrupt controllers), various I/O controller peripherals, and routing logic.

The processor(s) 610 may further include a safety cluster engine that includes a dedicated processor subsystem to handle safety management for automotive applications. The safety cluster engine may include two or more processor cores, a tightly coupled RAM, support peripherals (e.g., timers, an interrupt controller, etc.), and/or routing logic. In a safety mode, the two or more cores may operate in a lockstep mode and function as a single core with comparison logic to detect any differences between their operations.

The processor(s) 610 may further include a real-time camera engine that may include a dedicated processor subsystem for handling real-time camera management.

The processor(s) 610 may further include a high-dynamic range signal processor that may include an image signal processor that is a hardware engine that is part of the camera processing pipeline.

The processor(s) 610 may include a video image compositor that may be a processing block (e.g., implemented on a microprocessor) that implements video post-processing functions needed by a video playback application to produce the final image for the player window. The video image compositor may perform lens distortion correction on wide-view camera(s) 670, surround camera(s) 674, and/or on in-cabin monitoring camera sensors. In-cabin monitoring camera sensor is preferably monitored by a neural network running on another instance of the Advanced SoC, configured to identify in cabin events and respond accordingly. An in-cabin system may perform lip reading to activate cellular service and place a phone call, dictate emails, change the vehicle's destination, activate or change the vehicle's infotainment system and settings, or provide voice-activated web surfing. Certain functions are available to the driver only when the vehicle is operating in an autonomous mode, and are disabled otherwise.

The video image compositor may include enhanced temporal noise reduction for both spatial and temporal noise reduction. For example, where motion occurs in a video, the noise reduction weights spatial information appropriately, decreasing the weight of information provided by adjacent frames. Where an image or portion of an image does not include motion, the temporal noise reduction performed by the video image compositor may use information from the previous image to reduce noise in the current image.

The video image compositor may also be configured to perform stereo rectification on input stereo lens frames. The video image compositor may further be used for user interface composition when the operating system desktop is in use, and the GPU(s) 608 is not required to continuously render new surfaces. Even when the GPU(s) 608 is powered on and active doing 3D rendering, the video image compositor may be used to offload the GPU(s) 608 to improve performance and responsiveness.

The SoC(s) 604 may further include a mobile industry processor interface (MIPI) camera serial interface for receiving video and input from cameras, a high-speed interface, and/or a video input block that may be used for camera and related pixel input functions. The SoC(s) 604 may further include an input/output controller(s) that may be controlled by software and may be used for receiving I/O signals that are uncommitted to a specific role.

The SoC(s) 604 may further include a broad range of peripheral interfaces to enable communication with peripherals, audio codecs, power management, and/or other devices. The SoC(s) 604 may be used to process data from cameras (e.g., connected over Gigabit Multimedia Serial Link and Ethernet), sensors (e.g., LIDAR sensor(s) 664, RADAR sensor(s) 660, etc. that may be connected over Ethernet), data from bus 602 (e.g., speed of vehicle 600, steering wheel position, etc.), data from GNSS sensor(s) 658 (e.g., connected over Ethernet or CAN bus). The SoC(s) 604 may further include dedicated high-performance mass storage controllers that may include their own DMA engines, and that may be used to free the CPU(s) 606 from routine data management tasks.

The SoC(s) 604 may be an end-to-end platform with a flexible architecture that spans automation levels 3-5, thereby providing a comprehensive functional safety architecture that leverages and makes efficient use of computer vision and ADAS techniques for diversity and redundancy, provides a platform for a flexible, reliable driving software stack, along with deep learning tools. The SoC(s) 604 may be faster, more reliable, and even more energy-efficient and space-efficient than conventional systems. For example, the accelerator(s) 614, when combined with the CPU(s) 606, the GPU(s) 608, and the data store(s) 616, may provide for a fast, efficient platform for level 3-5 autonomous vehicles.

The technology thus provides capabilities and functionality that cannot be achieved by conventional systems. For example, computer vision algorithms may be executed on CPUs, which may be configured using high-level programming language, such as the C programming language, to execute a wide variety of processing algorithms across a wide variety of visual data. However, CPUs are oftentimes unable to meet the performance requirements of many computer vision applications, such as those related to execution time and power consumption, for example. In particular, many CPUs are unable to execute complex object detection algorithms in real-time, which is a requirement of in-vehicle ADAS applications, and a requirement for practical Level 3-5 autonomous vehicles.

In contrast to conventional systems, by providing a CPU complex, GPU complex, and a hardware acceleration cluster, the technology described herein allows for multiple neural networks to be performed simultaneously and/or sequentially, and for the results to be combined together to enable Level 3-5 autonomous driving functionality. For example, a CNN executing on the DLA or dGPU (e.g., the GPU(s) 620) may include a text and word recognition, allowing the supercomputer to read and understand traffic signs, including signs for which the neural network has not been specifically trained. The DLA may further include a neural network that is able to identify, interpret, and provides semantic understanding of the sign, and to pass that semantic understanding to the path planning modules running on the CPU Complex.

As another example, multiple neural networks may be run simultaneously, as is required for Level 3, 4, or 5 driving. For example, a warning sign consisting of "Caution: flashing lights indicate icy conditions," along with an electric light, may be independently or collectively interpreted by several neural networks. The sign itself may be identified as a traffic sign by a first deployed neural network (e.g., a neural network that has been trained), the text "Flashing lights indicate icy conditions" may be interpreted by a second deployed neural network, which informs the vehicle's path planning software (preferably executing on the CPU Complex) that when flashing lights are detected, icy conditions exist. The flashing light may be identified by operating a third deployed neural network over multiple frames, informing the vehicle's path-planning software of the presence (or absence) of flashing lights. All three neural networks may run simultaneously, such as within the DLA and/or on the GPU(s) 608.

In some examples, a CNN for facial recognition and vehicle owner identification may use data from camera sensors to identify the presence of an authorized driver and/or owner of the vehicle 600. The always on sensor processing engine may be used to unlock the vehicle when the owner approaches the driver door and turn on the lights, and, in security mode, to disable the vehicle when the owner leaves the vehicle. In this way, the SoC(s) 604 provide for security against theft and/or carjacking.

In another example, a CNN for emergency vehicle detection and identification may use data from microphones 696 to detect and identify emergency vehicle sirens. In contrast to conventional systems, that use general classifiers to detect sirens and manually extract features, the SoC(s) 604 use the CNN for classifying environmental and urban sounds, as well as classifying visual data. In a preferred embodiment, the CNN running on the DLA is trained to identify the relative closing speed of the emergency vehicle (e.g., by using the Doppler Effect). The CNN may also be trained to identify emergency vehicles specific to the local area in which the vehicle is operating, as identified by GNSS sensor(s) 658. Thus, for example, when operating in Europe the CNN will seek to detect European sirens, and when in the United States the CNN will seek to identify only North American sirens. Once an emergency vehicle is detected, a control program may be used to execute an emergency vehicle safety routine, slowing the vehicle, pulling over to the side of the road, parking the vehicle, and/or idling the vehicle, with the assistance of ultrasonic sensors 662, until the emergency vehicle(s) passes.

The vehicle may include a CPU(s) 618 (e.g., discrete CPU(s), or dCPU(s)), that may be coupled to the SoC(s) 604 via a high-speed interconnect (e.g., PCIe). The CPU(s) 618 may include an X86 processor, for example. The CPU(s) 618 may be used to perform any of a variety of functions, including arbitrating potentially inconsistent results between ADAS sensors and the SoC(s) 604, and/or monitoring the status and health of the controller(s) 636 and/or infotainment SoC 630, for example.

The vehicle 600 may include a GPU(s) 620 (e.g., discrete GPU(s), or dGPU(s)), that may be coupled to the SoC(s) 604 via a high-speed interconnect (e.g., NVIDIA's NVLINK). The GPU(s) 620 may provide additional artificial intelligence functionality, such as by executing redundant and/or different neural networks, and may be used to train and/or update neural networks based on input (e.g., sensor data) from sensors of the vehicle 600.

The vehicle 600 may further include the network interface 624 which may include one or more wireless antennas 626 (e.g., one or more wireless antennas for different communication protocols, such as a cellular antenna, a Bluetooth antenna, etc.). The network interface 624 may be used to enable wireless connectivity over the Internet with the cloud (e.g., with the server(s) 678 and/or other network devices), with other vehicles, and/or with computing devices (e.g., client devices of passengers). To communicate with other vehicles, a direct link may be established between the two vehicles and/or an indirect link may be established (e.g., across networks and over the Internet). Direct links may be provided using a vehicle-to-vehicle communication link. The vehicle-to-vehicle communication link may provide the vehicle 600 information about vehicles in proximity to the vehicle 600 (e.g., vehicles in front of, on the side of, and/or behind the vehicle 600). This functionality may be part of a cooperative adaptive cruise control functionality of the vehicle 600.

The network interface 624 may include a SoC that provides modulation and demodulation functionality and enables the controller(s) 636 to communicate over wireless networks. The network interface 624 may include a radio frequency front-end for up-conversion from baseband to radio frequency, and down conversion from radio frequency to baseband. The frequency conversions may be performed through well-known processes, and/or may be performed using super-heterodyne processes. In some examples, the radio frequency front end functionality may be provided by a separate chip. The network interface may include wireless functionality for communicating over LTE, WCDMA, UMTS, GSM, CDMA2000, Bluetooth, Bluetooth LE, Wi-Fi, Z-Wave, ZigBee, LoRaWAN, and/or other wireless protocols.

The vehicle 600 may further include data store(s) 628 which may include off-chip (e.g., off the SoC(s) 604) storage. The data store(s) 628 may include one or more storage elements including RAM, SRAM, DRAM, VRAM, Flash, hard disks, and/or other components and/or devices that may store at least one bit of data.

The vehicle 600 may further include GNSS sensor(s) 658. The GNSS sensor(s) 658 (e.g., GPS, assisted GPS sensors, differential GPS (DGPS) sensors, etc.), to assist in mapping, perception, occupancy grid generation, and/or path planning functions. Any number of GNSS sensor(s) 658 may be used, including, for example and without limitation, a GPS using a USB connector with an Ethernet to Serial (RS-232) bridge.

The vehicle 600 may further include RADAR sensor(s) 660. The RADAR sensor(s) 660 may be used by the vehicle 600 for long-range vehicle detection, even in darkness and/or severe weather conditions. RADAR functional safety levels may be ASIL B. The RADAR sensor(s) 660 may use the CAN and/or the bus 602 (e.g., to transmit data generated by the RADAR sensor(s) 660) for control and to access object tracking data, with access to Ethernet to access raw data in some examples. A wide variety of RADAR sensor types may be used. For example, and without limitation, the RADAR sensor(s) 660 may be suitable for front, rear, and side RADAR use. In some example, Pulse Doppler RADAR sensor(s) are used.

The RADAR sensor(s) 660 may include different configurations, such as long range with narrow field of view, short range with wide field of view, short range side coverage, etc. In some examples, long-range RADAR may be used for adaptive cruise control functionality. The long-range RADAR systems may provide a broad field of view realized by two or more independent scans, such as within a 250 m range. The RADAR sensor(s) 660 may help in distinguishing between static and moving objects, and may be used by ADAS systems for emergency brake assist and forward collision warning. Long-range RADAR sensors may include monostatic multimodal RADAR with multiple (e.g., six or more) fixed RADAR antennae and a high-speed CAN and FlexRay interface. In an example with six antennae, the central four antennae may create a focused beam pattern, designed to record the vehicle's 600 surroundings at higher speeds with minimal interference from traffic in adjacent lanes. The other two antennae may expand the field of view, making it possible to quickly detect vehicles entering or leaving the vehicle's 600 lane.

Mid-range RADAR systems may include, as an example, a range of up to 660 m (front) or 80 m (rear), and a field of view of up to 42 degrees (front) or 650 degrees (rear). Short-range RADAR systems may include, without limitation, RADAR sensors designed to be installed at both ends of the rear bumper. When installed at both ends of the rear bumper, such a RADAR sensor systems may create two beams that constantly monitor the blind spot in the rear and next to the vehicle.

Short-range RADAR systems may be used in an ADAS system for blind spot detection and/or lane change assist.

The vehicle 600 may further include ultrasonic sensor(s) 662. The ultrasonic sensor(s) 662, which may be positioned at the front, back, and/or the sides of the vehicle 600, may be used for park assist and/or to create and update an occupancy grid. A wide variety of ultrasonic sensor(s) 662 may be used, and different ultrasonic sensor(s) 662 may be used for different ranges of detection (e.g., 2.5 m, 4 m). The ultrasonic sensor(s) 662 may operate at functional safety levels of ASIL B.

The vehicle 600 may include LIDAR sensor(s) 664. The LIDAR sensor(s) 664 may be used for object and pedestrian detection, emergency braking, collision avoidance, and/or other functions. The LIDAR sensor(s) 664 may be functional safety level ASIL B. In some examples, the vehicle 600 may include multiple LIDAR sensors 664 (e.g., two, four, six, etc.) that may use Ethernet (e.g., to provide data to a Gigabit Ethernet switch).

In some examples, the LIDAR sensor(s) 664 may be capable of providing a list of objects and their distances for a 360-degree field of view. Commercially available LIDAR sensor(s) 664 may have an advertised range of approximately 600 m, with an accuracy of 2 cm-3 cm, and with support for a 600 Mbps Ethernet connection, for example. In some examples, one or more non-protruding LIDAR sensors 664 may be used. In such examples, the LIDAR sensor(s) 664 may be implemented as a small device that may be embedded into the front, rear, sides, and/or corners of the vehicle 600. The LIDAR sensor(s) 664, in such examples, may provide up to a 120-degree horizontal and 35-degree vertical field-of-view, with a 200 m range even for low-reflectivity objects. Front-mounted LIDAR sensor(s) 664 may be configured for a horizontal field of view between 45 degrees and 135 degrees.

In some examples, LIDAR technologies, such as 3D flash LIDAR, may also be used. 3D Flash LIDAR uses a flash of a laser as a transmission source, to illuminate vehicle surroundings up to approximately 200 m. A flash LIDAR unit includes a receptor, which records the laser pulse transit time and the reflected light on each pixel, which in turn corresponds to the range from the vehicle to the objects. Flash LIDAR may allow for highly accurate and distortion-free images of the surroundings to be generated with every laser flash. In some examples, four flash LIDAR sensors may be deployed, one at each side of the vehicle 600. Available 3D flash LIDAR systems include a solid-state 3D staring array LIDAR camera with no moving parts other than a fan (e.g., a non-scanning LIDAR device). The flash LIDAR device may use a 5 nanosecond class I (eye-safe) laser pulse per frame and may capture the reflected laser light in the form of 3D range point clouds and co-registered intensity data. By using flash LIDAR, and because flash LIDAR is a solid-state device with no moving parts, the LIDAR sensor(s) 664 may be less susceptible to motion blur, vibration, and/or shock.

The vehicle may further include IMU sensor(s) 666. The IMU sensor(s) 666 may be located at a center of the rear axle of the vehicle 600, in some examples. The IMU sensor(s) 666 may include, for example and without limitation, an accelerometer(s), a magnetometer(s), a gyroscope(s), a magnetic compass(es), and/or other sensor types. In some examples, such as in six-axis applications, the IMU sensor(s) 666 may include accelerometers and gyroscopes, while in nine-axis applications, the IMU sensor(s) 666 may include accelerometers, gyroscopes, and magnetometers.

In some embodiments, the IMU sensor(s) 666 may be implemented as a miniature, high performance GPS-Aided Inertial Navigation System (GPS/INS) that combines micro-electro-mechanical systems (MEMS) inertial sensors, a high-sensitivity GPS receiver, and advanced Kalman filtering algorithms to provide estimates of position, velocity, and attitude. As such, in some examples, the IMU sensor(s) 666 may enable the vehicle 600 to estimate heading without requiring input from a magnetic sensor by directly observing and correlating the changes in velocity from GPS to the IMU sensor(s) 666. In some examples, the IMU sensor(s) 666 and the GNSS sensor(s) 658 may be combined in a single integrated unit.

The vehicle may include microphone(s) 696 placed in and/or around the vehicle 600. The microphone(s) 696 may be used for emergency vehicle detection and identification, among other things.

The vehicle may further include any number of camera types, including stereo camera(s) 668, wide-view camera(s) 670, infrared camera(s) 672, surround camera(s) 674, long-range and/or mid-range camera(s) 698, and/or other camera types. The cameras may be used to capture image data around an entire periphery of the vehicle 600. The types of cameras used depends on the embodiments and requirements for the vehicle 600, and any combination of camera types may be used to provide the necessary coverage around the vehicle 600. In addition, the number of cameras may differ depending on the embodiment. For example, the vehicle may include six cameras, seven cameras, ten cameras, twelve cameras, and/or another number of cameras. The cameras may support, as an example and without limitation, Gigabit Multimedia Serial Link (GMSL) and/or Gigabit Ethernet. Each of the camera(s) is described with more detail herein with respect to FIG. 6A and FIG. 6B.

The vehicle 600 may further include vibration sensor(s) 642. The vibration sensor(s) 642 may measure vibrations of components of the vehicle, such as the axle(s). For example, changes in vibrations may indicate a change in road surfaces. In another example, when two or more vibration sensors 642 are used, the differences between the vibrations may be used to determine friction or slippage of the road surface (e.g., when the difference in vibration is between a power-driven axle and a freely rotating axle).

The vehicle 600 may include an ADAS system 638. The ADAS system 638 may include a SoC, in some examples. The ADAS system 638 may include autonomous/adaptive/automatic cruise control (ACC), cooperative adaptive cruise control (CACC), forward crash warning (FCW), automatic emergency braking (AEB), lane departure warnings (LDW), lane keep assist (LKA), blind spot warning (BSW), rear cross-traffic warning (RCTW), collision warning systems (CWS), lane centering (LC), and/or other features and functionality.

The ACC systems may use RADAR sensor(s) 660, LIDAR sensor(s) 664, and/or a camera(s). The ACC systems may include longitudinal ACC and/or lateral ACC. Longitudinal ACC monitors and controls the distance to the vehicle immediately ahead of the vehicle 600 and automatically adjust the vehicle speed to maintain a safe distance from vehicles ahead. Lateral ACC performs distance keeping, and advises the vehicle 600 to change lanes when necessary. Lateral ACC is related to other ADAS applications such as LCA and CWS.

CACC uses information from other vehicles that may be received via the network interface 624 and/or the wireless antenna(s) 626 from other vehicles via a wireless link, or indirectly, over a network connection (e.g., over the Internet). Direct links may be provided by a vehicle-to-vehicle (V2V) communication link, while indirect links may be infrastructure-to-vehicle (I2V) communication link. In general, the V2V communication concept provides information about the immediately preceding vehicles (e.g., vehicles immediately ahead of and in the same lane as the vehicle 600), while the I2V communication concept provides information about traffic further ahead. CACC systems may include either or both I2V and V2V information sources. Given the information of the vehicles ahead of the vehicle 600, CACC may be more reliable and it has potential to improve traffic flow smoothness and reduce congestion on the road.

FCW systems are designed to alert the driver to a hazard, so that the driver may take corrective action. FCW systems use a front-facing camera and/or RADAR sensor(s) 660, coupled to a dedicated processor, DSP, FPGA, and/or ASIC, that is electrically coupled to driver feedback, such as a display, speaker, and/or vibrating component. FCW systems may provide a warning, such as in the form of a sound, visual warning, vibration and/or a quick brake pulse.

AEB systems detect an impending forward collision with another vehicle or other object, and may automatically apply the brakes if the driver does not take corrective action within a specified time or distance parameter. AEB systems may use front-facing camera(s) and/or RADAR sensor(s) 660, coupled to a dedicated processor, DSP, FPGA, and/or ASIC. When the AEB system detects a hazard, it typically first alerts the driver to take corrective action to avoid the collision and, if the driver does not take corrective action, the AEB system may automatically apply the brakes in an effort to prevent, or at least mitigate, the impact of the predicted collision. AEB systems, may include techniques such as dynamic brake support and/or crash imminent braking.

LDW systems provide visual, audible, and/or tactile warnings, such as steering wheel or seat vibrations, to alert the driver when the vehicle 600 crosses lane markings. A LDW system does not activate when the driver indicates an intentional lane departure, by activating a turn signal. LDW systems may use front-side facing cameras, coupled to a dedicated processor, DSP, FPGA, and/or ASIC, that is electrically coupled to driver feedback, such as a display, speaker, and/or vibrating component.

LKA systems are a variation of LDW systems. LKA systems provide steering input or braking to correct the vehicle 600 if the vehicle 600 starts to exit the lane.

BSW systems detects and warn the driver of vehicles in an automobile's blind spot. BSW systems may provide a visual, audible, and/or tactile alert to indicate that merging or changing lanes is unsafe. The system may provide an additional warning when the driver uses a turn signal. BSW systems may use rear-side facing camera(s) and/or RADAR sensor(s) 660, coupled to a dedicated processor, DSP, FPGA, and/or ASIC, that is electrically coupled to driver feedback, such as a display, speaker, and/or vibrating component.

RCTW systems may provide visual, audible, and/or tactile notification when an object is detected outside the rear-camera range when the vehicle 600 is backing up. Some RCTW systems include AEB to ensure that the vehicle brakes are applied to avoid a crash. RCTW systems may use one or more rear-facing RADAR sensor(s) 660, coupled to a dedicated processor, DSP, FPGA, and/or ASIC, that is electrically coupled to driver feedback, such as a display, speaker, and/or vibrating component.

Conventional ADAS systems may be prone to false positive results which may be annoying and distracting to a driver, but typically are not catastrophic, because the ADAS systems alert the driver and allow the driver to decide whether a safety condition truly exists and act accordingly. However, in an autonomous vehicle 600, the vehicle 600 itself must, in the case of conflicting results, decide whether to heed the result from a primary computer or a secondary computer (e.g., a first controller 636 or a second controller 636). For example, in some embodiments, the ADAS system 638 may be a backup and/or secondary computer for providing perception information to a backup computer rationality module. The backup computer rationality monitor may run a redundant diverse software on hardware components to detect faults in perception and dynamic driving tasks. Outputs from the ADAS system 638 may be provided to a supervisory MCU. If outputs from the primary computer and the secondary computer conflict, the supervisory MCU must determine how to reconcile the conflict to ensure safe operation.

In some examples, the primary computer may be configured to provide the supervisory MCU with a confidence score, indicating the primary computer's confidence in the chosen result. If the confidence score exceeds a threshold, the supervisory MCU may follow the primary computer's direction, regardless of whether the secondary computer provides a conflicting or inconsistent result. Where the confidence score does not meet the threshold, and where the primary and secondary computer indicate different results (e.g., the conflict), the supervisory MCU may arbitrate between the computers to determine the appropriate outcome.

The supervisory MCU may be configured to run a neural network(s) that is trained and configured to determine, based on outputs from the primary computer and the secondary computer, conditions under which the secondary computer provides false alarms. Thus, the neural network(s) in the supervisory MCU may learn when the secondary computer's output may be trusted, and when it cannot. For example, when the secondary computer is a RADAR-based FCW system, a neural network(s) in the supervisory MCU may learn when the FCW system is identifying metallic objects that are not, in fact, hazards, such as a drainage grate or manhole cover that triggers an alarm. Similarly, when the secondary computer is a camera-based LDW system, a neural network in the supervisory MCU may learn to override the LDW when bicyclists or pedestrians are present and a lane departure is, in fact, the safest maneuver. In embodiments that include a neural network(s) running on the supervisory MCU, the supervisory MCU may include at least one of a DLA or GPU suitable for running the neural network(s) with associated memory. In preferred embodiments, the supervisory MCU may comprise and/or be included as a component of the SoC(s) 604.

In other examples, ADAS system 638 may include a secondary computer that performs ADAS functionality using traditional rules of computer vision. As such, the secondary computer may use classic computer vision rules (if-then), and the presence of a neural network(s) in the supervisory MCU may improve reliability, safety and performance. For example, the diverse implementation and intentional non-identity makes the overall system more fault-tolerant, especially to faults caused by software (or software-hardware interface) functionality. For example, if there is a software bug or error in the software running on the primary computer, and the non-identical software code running on the secondary computer provides the same overall result, the supervisory MCU may have greater confidence that the overall result is correct, and the bug in software or hardware on primary computer is not causing material error.

In some examples, the output of the ADAS system 638 may be fed into the primary computer's perception block and/or the primary computer's dynamic driving task block. For example, if the ADAS system 638 indicates a forward crash warning due to an object immediately ahead, the perception block may use this information when identifying objects. In other examples, the secondary computer may have its own neural network which is trained and thus reduces the risk of false positives, as described herein.

The vehicle 600 may further include the infotainment SoC 630 (e.g., an in-vehicle infotainment system (IVI)). Although illustrated and described as a SoC, the infotainment system may not be a SoC, and may include two or more discrete components. The infotainment SoC 630 may include a combination of hardware and software that may be used to provide audio (e.g., music, a personal digital assistant, navigational instructions, news, radio, etc.), video (e.g., TV, movies, streaming, etc.), phone (e.g., hands-free calling), network connectivity (e.g., LTE, Wi-Fi, etc.), and/or information services (e.g., navigation systems, rear-parking assistance, a radio data system, vehicle related information such as fuel level, total distance covered, brake fuel level, oil level, door open/close, air filter information, etc.) to the vehicle 600. For example, the infotainment SoC 630 may radios, disk players, navigation systems, video players, USB and Bluetooth connectivity, carputers, in-car entertainment, Wi-Fi, steering wheel audio controls, hands free voice control, a heads-up display (HUD), an HMI display 634, a telematics device, a control panel (e.g., for controlling and/or interacting with various components, features, and/or systems), and/or other components. The infotainment SoC 630 may further be used to provide information (e.g., visual and/or audible) to a user(s) of the vehicle, such as information from the ADAS system 638, autonomous driving information such as planned vehicle maneuvers, trajectories, surrounding environment information (e.g., intersection information, vehicle information, road information, etc.), and/or other information.

The infotainment SoC 630 may include GPU functionality. The infotainment SoC 630 may communicate over the bus 602 (e.g., CAN bus, Ethernet, etc.) with other devices, systems, and/or components of the vehicle 600. In some examples, the infotainment SoC 630 may be coupled to a supervisory MCU such that the GPU of the infotainment system may perform some self-driving functions in the event that the primary controller(s) 636 (e.g., the primary and/or backup computers of the vehicle 600) fail. In such an example, the infotainment SoC 630 may put the vehicle 600 into a chauffeur to safe stop mode, as described herein.

The vehicle 600 may further include an instrument cluster 632 (e.g., a digital dash, an electronic instrument cluster, a digital instrument panel, etc.). The instrument cluster 632 may include a controller and/or supercomputer (e.g., a discrete controller or supercomputer). The instrument cluster 632 may include a set of instrumentation such as a speedometer, fuel level, oil pressure, tachometer, odometer, turn indicators, gearshift position indicator, seat belt warning light(s), parking-brake warning light(s), engine-malfunction light(s), airbag (SRS) system information, lighting controls, safety system controls, navigation information, etc. In some examples, information may be displayed and/or shared among the infotainment SoC 630 and the instrument cluster 632. In other words, the instrument cluster 632 may be included as part of the infotainment SoC 630, or vice versa. The instrument cluster 632 may also include sensors (e.g., cameras) that may be used to capture sensor data such as images of a user's facial features. In some embodiments, the sensors may be used as ground truth locations for explicit calibration to generate one or more personalized calibration functions for a user.

Figure 6D:
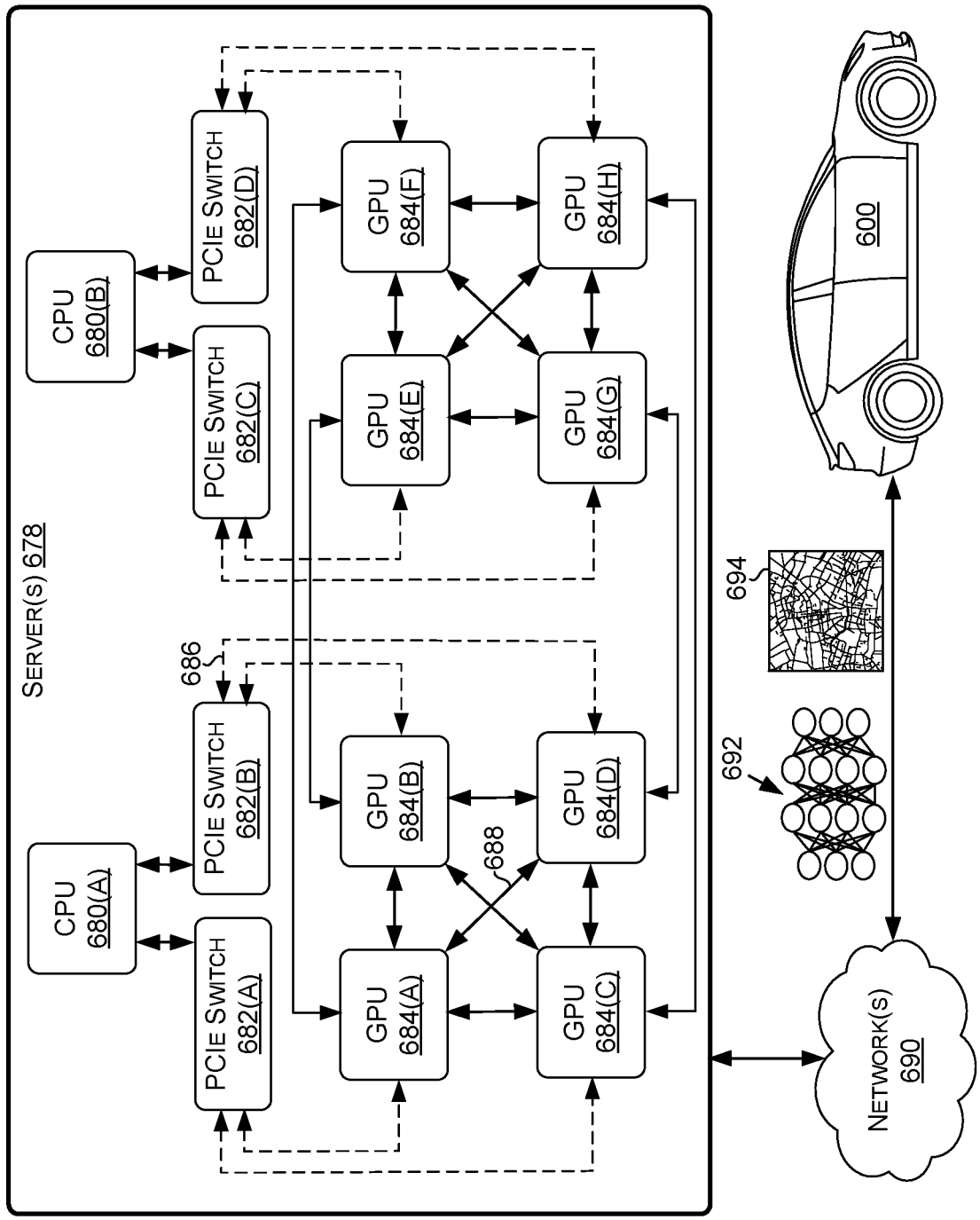
FIG. 6D is a system diagram for communication between cloud-based server(s) and the example autonomous vehicle of FIG. 6A, in accordance with some embodiments of the present disclosure.

FIG. 6D is a system diagram for communication between cloud-based server(s) and the example autonomous vehicle 600 of FIG. 6A, in accordance with some embodiments of the present disclosure. The system 676 may include server(s) 678, network(s) 690, and vehicles, including the vehicle 600. The server(s) 678 may include a plurality of GPUs 684(A)-684(H) (collectively referred to herein as GPUs 684), PCIe switches 682(A)-682(H) (collectively referred to herein as PCIe switches 682), and/or CPUs 680(A)-680(B) (collectively referred to herein as CPUs 680). The GPUs 684, the CPUs 680, and the PCIe switches may be interconnected with high-speed interconnects such as, for example and without limitation, NVLink interfaces 688 developed by NVIDIA and/or PCIe connections 686. In some examples, the GPUs 684 are connected via NVLink and/or NVSwitch SoC and the GPUs 684 and the PCIe switches 682 are connected via PCIe interconnects. Although eight GPUs 684, two CPUs 680, and two PCIe switches are illustrated, this is not intended to be limiting.

Depending on the embodiment, each of the server(s) 678 may include any number of GPUs 684, CPUs 680, and/or PCIe switches. For example, the server(s) 678 may each include eight, sixteen, thirty-two, and/or more GPUs 684.

The server(s) 678 may receive, over the network(s) 690 and from the vehicles, image data representative of images showing unexpected or changed road conditions, such as recently commenced road-work. The server(s) 678 may transmit, over the network(s) 690 and to the vehicles, neural networks 692, updated neural networks 692, and/or map information 694, including information regarding traffic and road conditions. The updates to the map information 694 may include updates for the HD map 622, such as information regarding construction sites, potholes, detours, flooding, and/or other obstructions. In some examples, the neural networks 692, the updated neural networks 692, and/or the map information 694 may have resulted from new training and/or experiences represented in data received from any number of vehicles in the environment, and/or based on training performed at a datacenter (e.g., using the server(s) 678 and/or other servers).

The server(s) 678 may be used to train machine learning models (e.g., neural networks) based on training data. The training data may be generated by the vehicles, and/or may be generated in a simulation (e.g., using a game engine). In some examples, the training data is tagged (e.g., where the neural network benefits from supervised learning) and/or undergoes other pre-processing, while in other examples the training data is not tagged and/or pre-processed (e.g., where the neural network does not require supervised learning). Training may be executed according to any one or more classes of machine learning techniques, including, without limitation, classes such as: supervised training, semi-supervised training, unsupervised training, self-learning, reinforcement learning, federated learning, transfer learning, feature learning (including principal component and cluster analyses), multi-linear subspace learning, manifold learning, representation learning (including spare dictionary learning), rule-based machine learning, anomaly detection, and any variants or combinations therefor. Once the machine learning models are trained, the machine learning models may be used by the vehicles (e.g., transmitted to the vehicles over the network(s) 690, and/or the machine learning models may be used by the server(s) 678 to remotely monitor the vehicles.

In some examples, the server(s) 678 may receive data from the vehicles and apply the data to up-to-date real-time neural networks for real-time intelligent inferencing. The server(s) 678 may include deep-learning supercomputers and/or dedicated AI computers powered by GPU(s) 684, such as a DGX and DGX Station machines developed by NVIDIA. However, in some examples, the server(s) 678 may include deep learning infrastructure that use only CPU-powered datacenters.

The deep-learning infrastructure of the server(s) 678 may be capable of fast, real-time inferencing, and may use that capability to evaluate and verify the health of the processors, software, and/or associated hardware in the vehicle 600. For example, the deep-learning infrastructure may receive periodic updates from the vehicle 600, such as a sequence of images and/or objects that the vehicle 600 has located in that sequence of images (e.g., via computer vision and/or other machine learning object classification techniques). The deep-learning infrastructure may run its own neural network to identify the objects and compare them with the objects identified by the vehicle 600 and, if the results do not match and the infrastructure concludes that the AI in the vehicle 600 is malfunctioning, the server(s) 678 may transmit a signal to the vehicle 600 instructing a fail-safe computer of the vehicle 600 to assume control, notify the passengers, and complete a safe parking maneuver.

For inferencing, the server(s) 678 may include the GPU(s) 684 and one or more programmable inference accelerators (e.g., NVIDIA's TensorRT). The combination of GPU-powered servers and inference acceleration may make real-time responsiveness possible. In other examples, such as where performance is less critical, servers powered by CPUs, FPGAs, and other processors may be used for inferencing.

Example Computing Device

Figure 7:
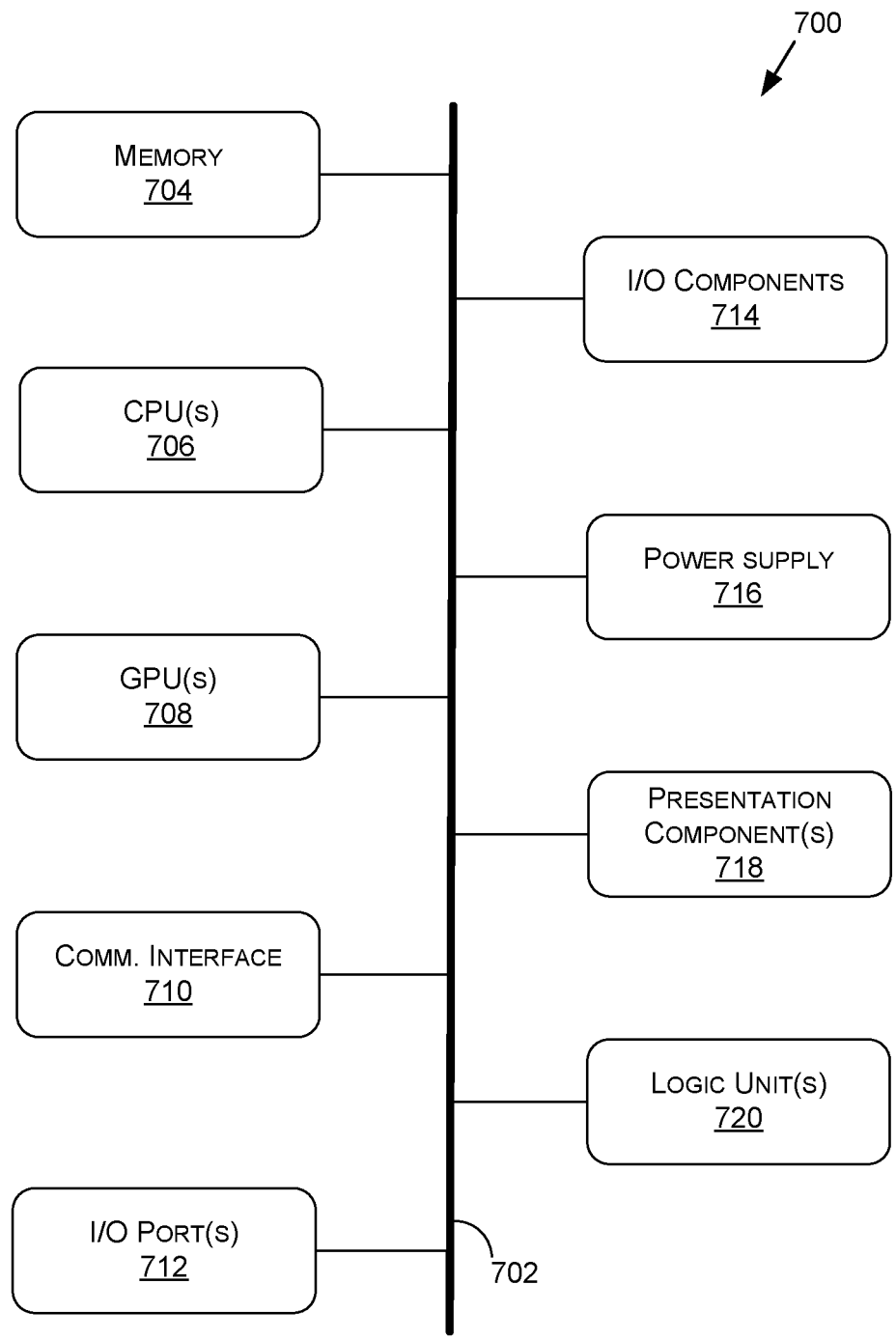
FIG. 7 is a block diagram of an example computing device suitable for use in implementing some embodiments of the present disclosure.

FIG. 7 is a block diagram of an example computing device(s) 700 suitable for use in implementing some embodiments of the present disclosure. Computing device 700 may include an interconnect system 702 that directly or indirectly couples the following devices: memory 704, one or more central processing units (CPUs) 706, one or more graphics processing units (GPUs) 708, a communication interface 710, input/output (I/O) ports 712, input/output components 714, a power supply 716, one or more presentation components 718 (e.g., display(s)), and one or more logic units 720. In at least one embodiment, the computing device(s) 700 may comprise one or more virtual machines (VMs), and/or any of the components thereof may comprise virtual components (e.g., virtual hardware components). For non-limiting examples, one or more of the GPUs 708 may comprise one or more vGPUs, one or more of the CPUs 706 may comprise one or more vCPUs, and/or one or more of the logic units 720 may comprise one or more virtual logic units. As such, a computing device(s) 700 may include discrete components (e.g., a full GPU dedicated to the computing device 700), virtual components (e.g., a portion of a GPU dedicated to the computing device 700), or a combination thereof.

Although the various blocks of FIG. 7 are shown as connected via the interconnect system 702 with lines, this is not intended to be limiting and is for clarity only. For example, in some embodiments, a presentation component 718, such as a display device, may be considered an I/O component 714 (e.g., if the display is a touch screen). As another example, the CPUs 706 and/or GPUs 708 may include memory (e.g., the memory 704 may be representative of a storage device in addition to the memory of the GPUs 708, the CPUs 706, and/or other components). In other words, the computing device of FIG. 7 is merely illustrative. Distinction is not made between such categories as "workstation," "server," "laptop," "desktop," "tablet," "client device," "mobile device," "hand-held device," "game console," "electronic control unit (ECU)," "virtual reality system," and/or other device or system types, as all are contemplated within the scope of the computing device of FIG. 7.

The interconnect system 702 may represent one or more links or busses, such as an address bus, a data bus, a control bus, or a combination thereof. The interconnect system 702 may include one or more bus or link types, such as an industry standard architecture (ISA) bus, an extended industry standard architecture (EISA) bus, a video electronics standards association (VESA) bus, a peripheral component interconnect (PCI) bus, a peripheral component interconnect express (PCIe) bus, and/or another type of bus or link. In some embodiments, there are direct connections between components. As an example, the CPU 706 may be directly connected to the memory 704. Further, the CPU 706 may be directly connected to the GPU 708. Where there is direct, or point-to-point connection between components, the interconnect system 702 may include a PCIe link to carry out the connection. In these examples, a PCI bus need not be included in the computing device 700.

The memory 704 may include any of a variety of computer-readable media. The computer-readable media may be any available media that may be accessed by the computing device 700. The computer-readable media may include both volatile and nonvolatile media, and removable and non-removable media. By way of example, and not limitation, the computer-readable media may comprise computer-storage media and communication media.

The computer-storage media may include both volatile and nonvolatile media and/or removable and non-removable media implemented in any method or technology for storage of information such as computer-readable instructions, data structures, program modules, and/or other data types. For example, the memory 704 may store computer-readable instructions (e.g., that represent a program(s) and/or a program element(s), such as an operating system. Computer-storage media may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by computing device 700. As used herein, computer storage media does not comprise signals per se.

The computer storage media may embody computer-readable instructions, data structures, program modules, and/or other data types in a modulated data signal such as a carrier wave or other transport mechanism and includes any information delivery media. The term "modulated data signal" may refer to a signal that has one or more of its characteristics set or changed in such a manner as to encode information in the signal. By way of example, and not limitation, the computer storage media may include wired media such as a wired network or direct-wired connection, and wireless media such as acoustic, RF, infrared and other wireless media. Combinations of any of the above should also be included within the scope of computer-readable media.

The CPU(s) 706 may be configured to execute at least some of the computer-readable instructions to control one or more components of the computing device 700 to perform one or more of the methods and/or processes described herein. The CPU(s) 706 may each include one or more cores (e.g., one, two, four, eight, twenty-eight, seventy-two, etc.) that are capable of handling a multitude of software threads simultaneously. The CPU(s) 706 may include any type of processor, and may include different types of processors depending on the type of computing device 700 implemented (e.g., processors with fewer cores for mobile devices and processors with more cores for servers). For example, depending on the type of computing device 700, the processor may be an Advanced RISC Machines (ARM) processor implemented using Reduced Instruction Set Computing (RISC) or an x86 processor implemented using Complex Instruction Set Computing (CISC). The computing device 700 may include one or more CPUs 706 in addition to one or more microprocessors or supplementary co-processors, such as math co-processors.

In addition to or alternatively from the CPU(s) 706, the GPU(s) 708 may be configured to execute at least some of the computer-readable instructions to control one or more components of the computing device 700 to perform one or more of the methods and/or processes described herein. One or more of the GPU(s) 708 may be an integrated GPU (e.g., with one or more of the CPU(s) 706 and/or one or more of the GPU(s) 708 may be a discrete GPU. In embodiments, one or more of the GPU(s) 708 may be a coprocessor of one or more of the CPU(s) 706. The GPU(s) 708 may be used by the computing device 700 to render graphics (e.g., 3D graphics) or perform general purpose computations. For example, the GPU(s) 708 may be used for General-Purpose computing on GPUs (GPGPU). The GPU(s) 708 may include hundreds or thousands of cores that are capable of handling hundreds or thousands of software threads simultaneously. The GPU(s) 708 may generate pixel data for output images in response to rendering commands (e.g., rendering commands from the CPU(s) 706 received via a host interface). The GPU(s) 708 may include graphics memory, such as display memory, for storing pixel data or any other suitable data, such as GPGPU data. The display memory may be included as part of the memory 704. The GPU(s) 708 may include two or more GPUs operating in parallel (e.g., via a link). The link may directly connect the GPUs (e.g., using NVLINK) or may connect the GPUs through a switch (e.g., using NVSwitch). When combined together, each GPU 708 may generate pixel data or GPGPU data for different portions of an output or for different outputs (e.g., a first GPU for a first image and a second GPU for a second image). Each GPU may include its own memory, or may share memory with other GPUs.

In addition to or alternatively from the CPU(s) 706 and/or the GPU(s) 708, the logic unit(s) 720 may be configured to execute at least some of the computer-readable instructions to control one or more components of the computing device 700 to perform one or more of the methods and/or processes described herein. In embodiments, the CPU(s) 706, the GPU(s) 708, and/or the logic unit(s) 720 may discretely or jointly perform any combination of the methods, processes and/or portions thereof. One or more of the logic units 720 may be part of and/or integrated in one or more of the CPU(s) 706 and/or the GPU(s) 708 and/or one or more of the logic units 720 may be discrete components or otherwise external to the CPU(s) 706 and/or the GPU(s) 708. In embodiments, one or more of the logic units 720 may be a coprocessor of one or more of the CPU(s) 706 and/or one or more of the GPU(s) 708.

Examples of the logic unit(s) 720 include one or more processing cores and/or components thereof, such as Tensor Cores (TCs), Tensor Processing Units (TPUs), Pixel Visual Cores (PVCs), Vision Processing Units (VPUs), Graphics Processing Clusters (GPCs), Texture Processing Clusters (TPCs), Streaming Multiprocessors (SMs), Tree Traversal Units (TTUs), Artificial Intelligence Accelerators (AIAs), Deep Learning Accelerators (DLAs), Arithmetic-Logic Units (ALUs), Application-Specific Integrated Circuits (ASICs), Floating Point Units (FPUs), input/output (I/O) elements, peripheral component interconnect (PCI) or peripheral component interconnect express (PCIe) elements, and/or the like.

The communication interface 710 may include one or more receivers, transmitters, and/or transceivers that enable the computing device 700 to communicate with other computing devices via an electronic communication network, included wired and/or wireless communications. The communication interface 710 may include components and functionality to enable communication over any of a number of different networks, such as wireless networks (e.g., Wi-Fi, Z-Wave, Bluetooth, Bluetooth LE, ZigBee, etc.), wired networks (e.g., communicating over Ethernet or InfiniBand), low-power wide-area networks (e.g., LoRaWAN, SigFox, etc.), and/or the Internet.

The I/O ports 712 may enable the computing device 700 to be logically coupled to other devices including the I/O components 714, the presentation component(s) 718, and/or other components, some of which may be built in to (e.g., integrated in) the computing device 700. Illustrative I/O components 714 include a microphone, mouse, keyboard, joystick, game pad, game controller, satellite dish, scanner, printer, wireless device, etc. The I/O components 714 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 700. In some embodiments, the NUI may process sensor data to identify facial features and detect facial landmark detection used to determine gaze predictions. The computing device 700 may be include depth cameras, such as stereoscopic camera systems, infrared camera systems, RGB camera systems, touchscreen technology, and combinations of these, for gesture detection and recognition. Additionally, the computing device 700 may include accelerometers or gyroscopes (e.g., as part of an inertia measurement unit (IMU)) that enable detection of motion. In some examples, the output of the accelerometers or gyroscopes may be used by the computing device 700 to render immersive augmented reality or virtual reality.

The power supply 716 may include a hard-wired power supply, a battery power supply, or a combination thereof. The power supply 716 may provide power to the computing device 700 to enable the components of the computing device 700 to operate.

The presentation component(s) 718 may include a display (e.g., a monitor, a touch screen, a television screen, a heads-up-display (HUD), other display types, or a combination thereof), speakers, and/or other presentation components. The presentation component(s) 718 may receive data from other components (e.g., the GPU(s) 708, the CPU(s) 706, etc.), and output the data (e.g., as an image, video, sound, etc.).

Example Data Center

Figure 8:
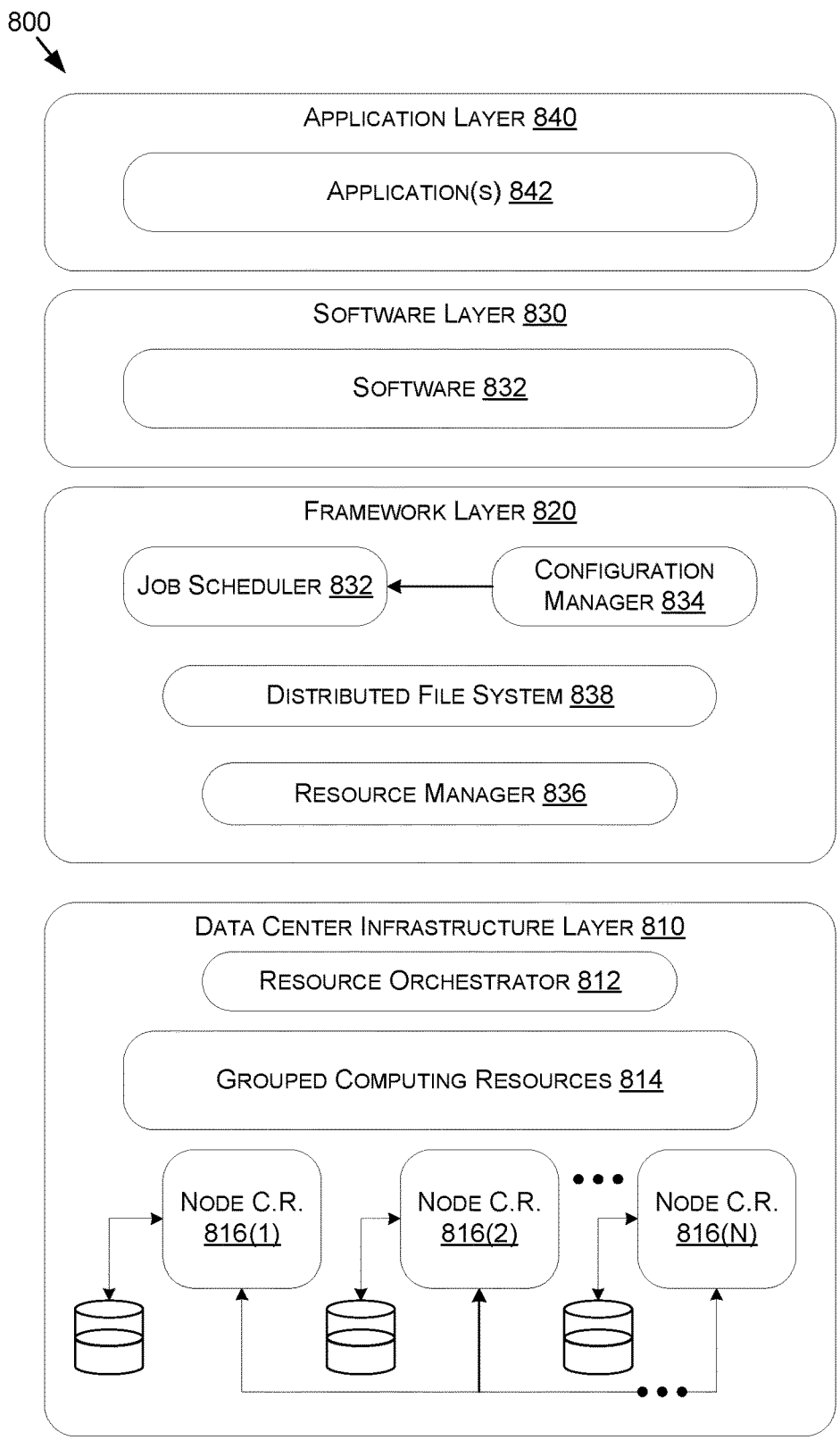
FIG. 8 is a block diagram of an example data center suitable for use in implementing some embodiments of the present disclosure.

FIG. 8 illustrates an example data center 800 that may be used in at least one embodiments of the present disclosure. The data center 800 may include a data center infrastructure layer 810, a framework layer 820, a software layer 830, and/or an application layer 840.

As shown in FIG. 8, the data center infrastructure layer 810 may include a resource orchestrator 812, grouped computing resources 814, and node computing resources ("node C.R.s") 816(1)-816(N), where "N" represents any whole, positive integer. In at least one embodiment, node C.R.s 816(1)-816(N) may include, but are not limited to, any number of central processing units ("CPUs") or other processors (including accelerators, field programmable gate arrays (FPGAs), graphics processors or graphics processing units (GPUs), etc.), memory devices (e.g., dynamic read-only memory), storage devices (e.g., solid state or disk drives), network input/output ("NW I/O") devices, network switches, virtual machines ("VMs"), power modules, and/or cooling modules, etc. In some embodiments, one or more node C.R.s from among node C.R.s 816(1)-816(N) may correspond to a server having one or more of the above-mentioned computing resources. In addition, in some embodiments, the node C.R.s 816(1)-8161(N) may include one or more virtual components, such as vGPUs, vCPUs, and/or the like, and/or one or more of the node C.R.s 816(1)-816(N) may correspond to a virtual machine (VM).

In at least one embodiment, grouped computing resources 814 may include separate groupings of node C.R.s 816 housed within one or more racks (not shown), or many racks housed in data centers at various geographical locations (also not shown). Separate groupings of node C.R.s 816 within grouped computing resources 814 may include grouped compute, network, memory or storage resources that may be configured or allocated to support one or more workloads. In at least one embodiment, several node C.R.s 816 including CPUs, GPUs, and/or other processors may be grouped within one or more racks to provide compute resources to support one or more workloads. The one or more racks may also include any number of power modules, cooling modules, and/or network switches, in any combination.

The resource orchestrator 822 may configure or otherwise control one or more node C.R.s 816(1)-816(N) and/or grouped computing resources 814. In at least one embodiment, resource orchestrator 822 may include a software design infrastructure ("SDI") management entity for the data center 800. The resource orchestrator 822 may include hardware, software, or some combination thereof.

In at least one embodiment, as shown in FIG. 8, framework layer 820 may include a job scheduler 832, a configuration manager 834, a resource manager 836, and/or a distributed file system 838. The framework layer 820 may include a framework to support software 832 of software layer 830 and/or one or more application(s) 842 of application layer 840. The software 832 or application(s) 842 may respectively include web-based service software or applications, such as those provided by Amazon Web Services, Google Cloud and Microsoft Azure. The framework layer 820 may be, but is not limited to, a type of free and open-source software web application framework such as Apache Spark™ (hereinafter "Spark") that may utilize distributed file system 838 for large-scale data processing (e.g., "big data"). In at least one embodiment, job scheduler 832 may include a Spark driver to facilitate scheduling of workloads supported by various layers of data center 800. The configuration manager 834 may be capable of configuring different layers such as software layer 830 and framework layer 820 including Spark and distributed file system 838 for supporting large-scale data processing. The resource manager 836 may be capable of managing clustered or grouped computing resources mapped to or allocated for support of distributed file system 838 and job scheduler 832. In at least one embodiment, clustered or grouped computing resources may include grouped computing resource 814 at data center infrastructure layer 810. The resource manager 1036 may coordinate with resource orchestrator 812 to manage these mapped or allocated computing resources.

In at least one embodiment, software 832 included in software layer 830 may include software used by at least portions of node C.R.s 816(1)-816(N), grouped computing resources 814, and/or distributed file system 838 of framework layer 820. One or more types of software may include, but are not limited to, Internet web page search software, e-mail virus scan software, database software, and streaming video content software.

In at least one embodiment, application(s) 842 included in application layer 840 may include one or more types of applications used by at least portions of node C.R.s 816(1)-816(N), grouped computing resources 814, and/or distributed file system 838 of framework layer 820. One or more types of applications may include, but are not limited to, any number of a genomics application, a cognitive compute, and a machine learning application, including training or inferencing software, machine learning framework software (e.g., PyTorch, TensorFlow, Caffe, etc.), and/or other machine learning applications used in conjunction with one or more embodiments.

In at least one embodiment, any of configuration manager 834, resource manager 836, and resource orchestrator 812 may implement any number and type of self-modifying actions based on any amount and type of data acquired in any technically feasible fashion. Self-modifying actions may relieve a data center operator of data center 800 from making possibly bad configuration decisions and possibly avoiding underutilized and/or poor performing portions of a data center.

The data center 800 may include tools, services, software or other resources to train one or more machine learning models or predict or infer information using one or more machine learning models according to one or more embodiments described herein. For example, a machine learning model(s) may be trained by calculating weight parameters according to a neural network architecture using software and/or computing resources described above with respect to the data center 800. In at least one embodiment, trained or deployed machine learning models corresponding to one or more neural networks may be used to infer or predict information using resources described above with respect to the data center 800 by using weight parameters calculated through one or more training techniques, such as but not limited to those described herein.

In at least one embodiment, the data center 800 may use CPUs, application-specific integrated circuits (ASICs), GPUs, FPGAs, and/or other hardware (or virtual compute resources corresponding thereto) to perform training and/or inferencing using above-described resources. Moreover, one or more software and/or hardware resources described above may be configured as a service to allow users to train or performing inferencing of information, such as image recognition, speech recognition, or other artificial intelligence services.

Example Network Environments

Network environments suitable for use in implementing embodiments of the disclosure may include one or more client devices, servers, network attached storage (NAS), other backend devices, and/or other device types. The client devices, servers, and/or other device types (e.g., each device) may be implemented on one or more instances of the computing device(s) 700 of FIG. 7—e.g., each device may include similar components, features, and/or functionality of the computing device(s) 700. In addition, where backend devices (e.g., servers, NAS, etc.) are implemented, the backend devices may be included as part of a data center 800, an example of which is described in more detail herein with respect to FIG. 8.

Components of a network environment may communicate with each other via a network(s), which may be wired, wireless, or both. The network may include multiple networks, or a network of networks. By way of example, the network may include one or more Wide Area Networks (WANs), one or more Local Area Networks (LANs), one or more public networks such as the Internet and/or a public switched telephone network (PSTN), and/or one or more private networks. Where the network includes a wireless telecommunications network, components such as a base station, a communications tower, or even access points (as well as other components) may provide wireless connectivity.

Compatible network environments may include one or more peer-to-peer network environments—in which case a server may not be included in a network environment—and one or more client-server network environments—in which case one or more servers may be included in a network environment. In peer-to-peer network environments, functionality described herein with respect to a server(s) may be implemented on any number of client devices.

In at least one embodiment, a network environment may include one or more cloud-based network environments, a distributed computing environment, a combination thereof, etc. A cloud-based network environment may include a framework layer, a job scheduler, a resource manager, and a distributed file system implemented on one or more of servers, which may include one or more core network servers and/or edge servers. A framework layer may include a framework to support software of a software layer and/or one or more application(s) of an application layer. The software or application(s) may respectively include web-based service software or applications. In embodiments, one or more of the client devices may use the web-based service software or applications (e.g., by accessing the service software and/or applications via one or more application programming interfaces (APIs)). The framework layer may be, but is not limited to, a type of free and open-source software web application framework such as that may use a distributed file system for large-scale data processing (e.g., "big data").

A cloud-based network environment may provide cloud computing and/or cloud storage that carries out any combination of computing and/or data storage functions described herein (or one or more portions thereof). Any of these various functions may be distributed over multiple locations from central or core servers (e.g., of one or more data centers that may be distributed across a state, a region, a country, the globe, etc.). If a connection to a user (e.g., a client device) is relatively close to an edge server(s), a core server(s) may designate at least a portion of the functionality to the edge server(s). A cloud-based network environment may be private (e.g., limited to a single organization), may be public (e.g., available to many organizations), and/or a combination thereof (e.g., a hybrid cloud environment).

The client device(s) may include at least some of the components, features, and functionality of the example computing device(s) 700 described herein with respect to FIG. 7. By way of example and not limitation, a client device may be embodied as a Personal Computer (PC), a laptop computer, a mobile device, a smartphone, a tablet computer, a smart watch, a wearable computer, a Personal Digital Assistant (PDA), an MP3 player, a virtual reality headset, a Global Positioning System (GPS) or device, a video player, a video camera, a surveillance device or system, a vehicle, a boat, a flying vessel, a virtual machine, a drone, a robot, a handheld communications device, a hospital device, a gaming device or system, an entertainment system, a vehicle computer system, an embedded system controller, a remote control, an appliance, a consumer electronic device, a workstation, an edge device, any combination of these delineated devices, or any other suitable device.

The disclosure may be described in the general context of computer code or machine-useable instructions, including computer-executable instructions such as program modules, being executed by a computer or other machine, such as a personal data assistant or other handheld device. Generally, program modules including routines, programs, objects, components, data structures, etc., refer to code that perform particular tasks or implement particular abstract data types. The disclosure may be practiced in a variety of system configurations, including hand-held devices, consumer electronics, general-purpose computers, more specialty computing devices, etc. The disclosure may also be practiced in distributed computing environments where tasks are performed by remote-processing devices that are linked through a communications network.

As used herein, a recitation of "and/or" with respect to two or more elements should be interpreted to mean only one element, or a combination of elements. For example, "element A, element B, and/or element C" may include only element A, only element B, only element C, element A and element B, element A and element C, element B and element C, or elements A, B, and C. In addition, "at least one of element A or element B" may include at least one of element A, at least one of element B, or at least one of element A and at least one of element B. Further, "at least one of element A and element B" may include at least one of element A, at least one of element B, or at least one of element A and at least one of element B.

The subject matter of the present disclosure is described with specificity herein to meet statutory requirements. However, the description itself is not intended to limit the scope of this disclosure. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

What is claimed is:

1. A method comprising:
   computing, using one or more machine learning models and based at least on sensor data generated using one or more sensors of a machine in an environment, one or more values indicative of a gaze of a user, one or more regions of the environment comprising at least one region calibrated using one or more calibration functions;
   determining, using the one or more values and based at least on one or more distances between the gaze and the one or more regions in the environment, that a gaze direction of the user is directed toward the one or more regions;
   selecting the one or more regions based at least on the determining the gaze direction is directed toward the one or more regions;
   selecting the one or more calibration functions for the gaze based at least on the selecting of the one or more regions;
   computing the one or more calibration functions using the one or more values to generate one or more updated values indicative of the gaze;
   determining one or more gaze locations of the user based at least on the one or more updated values; and
   performing one or more control operations for the machine based at least on the one or more gaze locations.

2. The method of claim 1, wherein the one or more values correspond to a three-dimensional (3D) location within the environment of the user, the one or more updated values correspond to an updated 3D location within the environment of the user, and the one or more gaze locations correspond to the updated 3D location.

3. The method of claim 1, wherein the selecting the one or more calibration functions includes selecting the one or more calibration functions from a plurality of calibration functions corresponding to different regions in the environment, and the selecting the one or more calibration functions is further based at least on determining the gaze falls within the one or more regions.

4. The method of claim 1, wherein the one or more values are indicative of at least one of a gaze vector or an angular offset, and the method further comprises:
   determining, based at least on the sensor data or other additional sensor data, a gaze origin of the user,
   wherein the determining the one or more gaze locations is further based at least on the gaze origin.

5. The method of claim 4, further comprising:
   identifying, based at least on the sensor data or the other additional sensor data, facial landmarks of the user,
   wherein the determining the gaze origin of the user is based at least on the identifying the facial landmarks.

6. The method of claim 1, further comprising prior to computing the one or more values, generating an assignment of the one or more calibration functions to the one or more regions based at least on a frequency of gazes associated with the one or more regions, wherein the selecting of the one or more calibration functions is further based at least on the assignment of the one or more calibration functions to the one or more regions.

7. The method of claim 1, wherein the selecting the one or more regions is further based at least on determining one or more triggering events corresponding to one or more actuations of the machine, the one or more triggering events associated with the one or more regions.

8. The method of claim 1, wherein the one or more calibration functions are generated, at least in part, by:
   determining an offset between ground truth locations within the environment of the user and computed locations within the environment of the user determined based at least on outputs of the one or more machine learning models; and
   generating the one or more calibration functions based at least on the offset.

9. The method of claim 8, wherein the one or more calibration functions are generated responsive to identifying that the user is gazing toward a calibration region, the calibration region included in the one or more regions.

10. The method of claim 9, wherein the calibration region is identified for generating the one or more calibration functions using one or more gaze saliency maps.

11. The method of claim 1, wherein the one or more calibration functions are updated during operation based at least on training sensor data generated while the user is gazing toward at least one of a calibration region or a calibration point.

12. The method of claim 1, wherein the one or more control operations correspond to one or more of redirecting the user to a potential hazard, steering the machine, reducing a velocity of the machine, or adjusting a position of the machine.

13. A system comprising:
one or more processing units to execute operations comprising:
- computing, using one or more machine learning models and based at least on sensor data generated using one or more sensors of a machine in an environment, one or more values indicative of a gaze of a user, one or more regions of the environment comprising at least one region calibrated using one or more calibration functions;
- determining, using the one or more values and based at least on one or more distances between the gaze and the one or more regions in the environment, that a gaze direction of the user is directed toward the one or more regions;
- selecting the one or more regions based at least on the determining the gaze direction is directed toward the one or more regions;
- selecting the one or more calibration functions for the gaze based at least on the selecting of the one or more regions;
- based at least on the selecting of the one or more calibration functions, applying the one or more calibration functions corresponding to the user to the one or more values to generate one or more updated values indicative of the gaze;
- determining one or more gaze locations of the user based at least on the one or more updated values; and
- performing one or more control operations for the machine based at least on the one or more gaze locations.

14. The system of claim 13, wherein the selecting the one or more regions includes identifying the one or more regions based at least on determining, using the sensor data or additional sensor data, that the gaze of the user falls within the one or more regions, and wherein the selecting the one or more calibration functions is further based at least on the determining the gaze of the user falls within the one or more regions.

15. The system of claim 13, wherein the one or more calibration functions are generated, at least in part, by:
- identifying the one or more regions;
- based at least on the identifying of the one or more regions, determining an offset between ground truth locations corresponding to the one or more regions within the environment of the user and computed locations within the environment of the user determined based at least in part on outputs of the one or more machine learning models; and
- generating the one or more calibration functions for the one or more regions based at least on the offset.

16. The system of claim 15, wherein the computed locations are computed based at least on training sensor data generated responsive to at least one of:
- prompting the user to gaze toward the ground truth locations; or
- identifying that the user is gazing toward at least one of a calibration region including in the one or more regions or a calibration point corresponding to the one or more regions.

17. The system of claim 13, wherein the system is comprised in at least one of:
- a control system for an autonomous or semi-autonomous machine;
- a perception system for an autonomous or semi-autonomous machine;
- a system for performing simulation operations;
- a system for performing deep learning operations;
- a system implemented using an edge device;
- a system implemented using a robot;
- a system incorporating one or more virtual machines (VMs);
- a system implemented at least partially in a data center; or
- a system implemented at least partially using cloud computing resources.

18. A processor comprising:
one or more circuits to:
- compute, using one or more machine learning models and based at least on sensor data obtained using one or more sensors of a machine in an environment, one or more values indicative of a gaze of a user, one or more regions of the environment comprising at least one region calibrated using one or more calibration functions;
- determine, using the one or more values and based at least on one or more distances between the gaze and one or more regions in an environment of the user, that a gaze direction of the user is directed toward the one or more regions;
- select the one or more regions based at least on the determining the gaze direction is directed toward the one or more regions;
- select the one or more calibration functions for the gaze based at least on the selecting of the one or more regions;
- based at least on the selecting of the one or more calibration functions, applying the one or more calibration functions corresponding to the user to the one or more values to generate one or more updated values indicative of the gaze;
- determine one or more gaze locations of the user based at least on the one or more updated values; and
- perform one or more control operations for the machine based at least on the one or more gaze locations.

19. The processor of claim 18, wherein the selecting the one or more regions is further based at least on determining one or more triggering events corresponding to one or more actuations of the machine, the one or more triggering events associated with the one or more regions.

20. The processor of claim 18, wherein the one or more circuits are further to define the one or more regions based at least on generating gaze saliency maps based at least on at least one of gaze patterns or gaze behaviors of one or more users.

21. The processor of claim 18, wherein the one or more control operations correspond to one or more of redirecting the user to a potential hazard, steering the machine, reducing a velocity of the machine, or adjusting a position of the machine.

22. The processor of claim 18, wherein the one or more circuits are further to, in deployment, update values of the one or more machine learning models by applying the one or more calibration functions to the one or more values.

23. The processor of claim 18, wherein the one or more values correspond to output values of the one or more machine learning models or values of a last layer of the one or more machine learning models.

* * * * *